US012760357B2

(12) United States Patent
Shi et al.

(10) Patent No.: US 12,760,357 B2
(45) Date of Patent: Oct. 13, 2026

(54) SYSTEM AND METHOD FOR TISSUE-WIDE SINGLE CELL POST-TRANSCRIPTIONAL PROFILING OF MULTIPLE MOLECULAR TARGETS

(71) Applicant: City University of Hong Kong, Hong Kong (CN)

(72) Inventors: Peng Shi, Hong Kong (CN); Xianglin Ji, Hong Kong (CN)

(73) Assignee: City Unversity of Hong Kong, Hong Kong (CN)

( * ) Notice: Subject to any disclaimer, the term of this patent is extended or adjusted under 35 U.S.C. 154(b) by 1024 days.

(21) Appl. No.: 17/931,942

(22) Filed: Sep. 14, 2022

(65) Prior Publication Data

US 2024/0093276 A1 Mar. 21, 2024

(51) Int. Cl.
*C12Q 1/6841* (2018.01)
*C12Q 1/6804* (2018.01)

(52) U.S. Cl.
CPC ......... *C12Q 1/6841* (2013.01); *C12Q 1/6804* (2013.01); *C12Q 2600/16* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 7,473,767 | B2 | 1/2009 | Dimitrov | |
| 2019/0226024 | A1* | 7/2019 | Shi | C12Q 1/686 |
| 2022/0073974 | A1 | 3/2022 | Gennaro | |
| 2025/0115947 | A1 | 4/2025 | Fan et al. | |

FOREIGN PATENT DOCUMENTS

| | | |
|---|---|---|
| WO | 2021076928 A1 | 4/2021 |

OTHER PUBLICATIONS

Liu (ACS Nano 2022 16 pp. 6916-6928).*
Portu (Reports of Practical Oncology and Radiotherapy 2016 vol. 21 pp. 129-134).*
Lubeck (Nature Methods vol. 9 No Jul. 7, 2012).*
Carney (Annals of the American Thoracic Society 20156 vol. 12 Issue 3).*
G K Geiss et al., "Direct multiplexed measurement of gene expression with color-coded probe pairs", Nature Biotechnology (2008), vol. 26 No.3.
C R Merritt et al., "Multiplex digital spatial profiling of proteins and RNA in fixed tissue", Nature Biotechnology, vol. 38, May 2020, 586-599.
Chen et al., "Spatial Transcriptomics and In Situ Sequencing to Study Alzheimer's Disease", Cell 182, 976-991, Aug. 20, 2020.
R Pinaud et al., "Detection of two mRNA species at single-cell resolution by double-fluorescence in situ hybridization", Nature Protocols (2008), vol. 3 No.8.
S Codeluppi et al., "Spatial organization of the somatosensory cortex revealed by osmFISH", Nature Methods (2018), vol. 15, 932-935.
Goh et al., "Highly specific multiplexed RNA imaging in tissues with split-FISH", Nature Methods (2020) vol. 17, 689-693.
K H Chen et al., "Spatially resolved, highly multiplexed RNA profiling in single cells", Science sciencemag.org, Apr. 24, 2015, vol. 348 Issue 6233 aaa6090-1.
E Lubeck et al., "Single-cell in situ RNA profiling by sequential hybridization", Nature Methods (2014) vol. 11 No. 4.
Eng et al., "Transcriptome-scale super-resolved imaging in tissues by RNA seqFISH+", Nature (2019), vol. 568.
Y Liu et al., "High-Spatial-Resolution Multi-Omics Sequencing via Deterministic Barcoding in Tissue", Cell 183, 1665-1681, Dec. 10, 2020.
S G Rodriques et al., "Slide-seq: A scalable technology for measuring genome-wide expression at high spatial resolution" Science 363, 1463-1467 (2019).
S Vickovic et al., "High-definition spatial transcriptomics for in situ tissue profiling", Nature Methods (2019), vol. 16, 987-990.
S R Srivatsan et al., "Embryo-scale, single-cell spatial transcriptomics", Science (2021) 373, 111-117.
F Hildebrandt et al., "Spatial Transcriptomics to define transcriptional patterns of zonation and structural components in the mouse liver", Nature Communications (2021), 12:7046.
L Bergenstrahle et al., "Super-resolved spatial transcriptomics by deep data fusion",Nature Biotechnology, www.nature.com/naturebiotechnology.
H Chen et al., "Dissecting mammalian spermatogenesis using spatial transcriptomics", Cell Reports 37, 109915, Nov. 2, 2021.
M B Nagarajan et al., "Spatially resolved and multiplexed MicroRNA quantification from tissue using nanoliter well arrays", Microsystems & Nanoengineering ( 2020) 6:51.
C R Merritt et al., "Multiplex digital spatial profiling of proteins and RNA in fixed tissue", Nature Biotechnology (2020), vol. 38 586, 586-599.

(Continued)

*Primary Examiner* — Amanda Haney
(74) *Attorney, Agent, or Firm* — S&F/WEHRW

(57) ABSTRACT

The present invention provides a platform for large-scale profiling of post-transcriptional molecular targets including microRNAs (miRNAs) and methylated messenger RNAs (such as $m^6A$ mRNAs) with subcellular spatial resolution in a tissue-wide scale. The present platform is capable of high-throughput isolation of intracellular molecules by contacting an array of functionalized nanoprobes with a target tissue sample for capturing the molecular targets, and the isolated molecular targets are in-situ analysed. The present invention also provides a spectrum barcoding system and related method for digitally quantifying the isolated molecular targets on the nanoprobes and mapping with an imprint of the tissue sample to provide a single-cell spatial coordinate and expression pattern of each of the molecular targets corresponding to different sub-regions of the tissue sample.

7 Claims, 25 Drawing Sheets
(25 of 25 Drawing Sheet(s) Filed in Color)

Specification includes a Sequence Listing.

(56) References Cited

OTHER PUBLICATIONS

T Chen et al., "m6A RNA Methylation Is Regulated by MicroRNAs and Promotes Reprogramming to Pluripotency", Cell Stem Cell 16, 289-301, Mar. 5, 2015.
T Annese et al., "microRNAs Biogenesis, Functions and Role in Tumor Angiogenesis", Frontiers in Oncology (2020), vol. 10, Article 581007.
M Chang et al., "Region-specific RNA m6A methylation represents a new layer of control in the gene regulatory network in the mouse brain", Open Biol. 7:170166.
J Liu et al., "Landscape and Regulation of m6A andm6Am Methylome across Human and Mouse Tissues", Molecular Cell 77, 426-440, Jan. 16, 2020.
Z Wang et al., "Interrogation of Cellular Innate Immunity by Diamond-Nanoneedle-Assisted Intracellular Molecular Fishing", Nano Lett. 2015, 15, 7058-7063.
Z Wang et al., "High-throughput intracellular biopsy of microRNAs for dissecting the temporal dynamics of cellular heterogeneity", Sci. Adv. 2020; 6 : eaba4971.
K Xie et al., "Profiling MicroRNAs with Associated Spatial Dynamics in Acute Tissue Slices", ACS Nano 2021, 15, 4881-4892.
E S Lein et al., "Genome-wide atlas of gene expression in the adult mouse brain", Nature (2007), vol. 445.
S Nagayama et al., "Neuronalorganizationofolfactorybulbcircuits", FrontiersinNeuralCircuits (2014), vol. 8 , Article 98.
R Petri et al., "let-7 regulates radial migration of new-born neurons through positive regulation of autophagy", The EMBO Journal (2017) 36: 1379-1391.
E Zhao et al., "Spatial transcriptomics at subspot resolution with BayesSpace", Nature Biotechnology (2021), vol. 39, 1375-1384.
A M Shafik et al., "N6-methyladenosine dynamics in neurodevelopment and aging, and its potential role in Alzheimer's disease", Genome Biology (2021) 22:17.
Z Zhang et al., "METTL3-mediated N6-methyladenosine mRNA modification enhances long-term memory consolidation", Cell Research (2018) 28:1050-1061.
X Chen et al., "Down-Regulation of m6A mRNA Methylation Is Involved in Dopaminergic Neuronal Death", ACS Chem. Neurosci. 2019, 10, 2355-2363.
M D Wilkerson et al., "ConsensusClusterPlus: a class discovery tool with confidence assessments and item tracking", Bioinformatics, vol. 26 No. 12 2010, pp. 1572-1573, doi:10.1093/bioinformatics/btq170.
E S Lein et al., "Genome-wide atlas of gene expression in the adult mouse brain", Nature (2007), vol. 445, doi:10.1038/nature05453.
Y Tang et al., "m6A-Atlas: a comprehensive knowledgebase for unraveling the N6-methyladenosine (m6A) epitranscriptome", Nucleic Acids Research (2021), vol. 49, Database issue.
Eng et al., "Profiling the transcriptome with RNA SPOTs", Nature Methods (2017), vol. 14, 1153.
Stahl et al., "Visualization and analysis of gene expression in tissue sections by spatial transcriptomics", Science sciencemag.org, Jul. 1, 2016, vol. 353 Issue 6294.

* cited by examiner

SYSTEM AND METHOD FOR TISSUE-WIDE SINGLE CELL POST-TRANSCRIPTIONAL PROFILING OF MULTIPLE MOLECULAR TARGETS

REFERENCE TO SEQUENCE DISCLOSURE

The sequence listing file under the file name "Sequence_Listing_034689-000048.xml" submitted in ST.26 XML file format with a file size of 93 KB created on Sep. 13, 2022 and filed on Sep. 14, 2022 is incorporated herein by reference.

TECHNICAL FIELD

The present invention relates to a system for correlated spatial analysis of multiple post-transcriptional regulations in single cell at a tissue-wide scale, in particular, a post-transcriptional regulation-specific molecular fishing platform in combination with a digital spectrum fluorescent in-situ hybridization (Spectrum-FISH) barcoding system to realize high throughput, large-scale profiling of post-transcriptional regulations with subcellular spatial resolution across an acute tissue biopsy.

BACKGROUND

Spatial heterogeneity in gene expression is closely related to human physiology in normal or diseased conditions. Different techniques have been evolved for capturing spatial information with cellular resolution across tissues to study critical genetic or epigenetic regulations among large-scale cellular populations. Among those techniques, fluorescence in-situ hybridization (FISH) has been widely used to assess the spatial distribution of mRNAs, in which different encoding strategies have been incorporated to enable high multiplexed analysis of mRNAs, where MERFISH (multiplexed error-robust FISH) is one of those using a combinatorial labeling strategy with an error-robust algorithm for simultaneous imaging of over 100 RNA species in a single cell. Another advanced FISH technique is sequential fluorescence in-situ hybridization (SeqFISH) for sequential analysis of different RNAs through multiple rounds of hybridization to increase the assay throughput. However, for profiling heterogeneous molecular targets of a tissue-wide sample, conventional FISH-based profiling techniques can not meet such a need because the conventional techniques mostly focus on subcellular localization of genetic targets and only limited to individual cells. Some of the conventional techniques even require super-resolution imaging aids, which limit their applications.

A large-scale, tissue-wide spatial transcriptomics by using an array of poly(T) tails to capture released mRNAs from a pre-treated tissue sample on a grid of spatially-indexed coordinates has been developed recently to attempt to meet such a demand. The captured mRNAs by such spatial transcriptomic method are subsequently identified by sequencing. However, such method involves a complex pre-treatment of the tissue, including frozen sectioning, fixation, membrane penetration, etc., to release intracellular mRNAs, which is laborious and time-consuming, and also easily leads to cross-contamination among adjacent regions and RNA degradation within certain spatial extent, in turn reducing spatial resolution of the associated transcriptomic analysis.

In addition, the majority of the conventional tissue-wide spatial profiling techniques are only limited to transcriptional (mRNAs), proteomic targets or chromatin modification, and seldom for analyzing tissue-wide post-transcriptional regulations. In terms of the post-transcriptional regulations, microRNAs (miRNAs) and methylated RNAs are two prevalent mechanisms closely related to complex gene expression topology for accommodating substantial regulatory flexibility, diversity, and robustness, where miRNAs are non-coding single-stranded small RNA molecules with about 21-23 nucleotides that modulate gene expression by inhibiting mRNA translation; RNA methylation is the most commonly found modification on mRNAs for regulating their metabolism. For example, $N^6$-methyladenosine ($m^6A$) modification is highly enriched in the mammalian brain, and distinct $m^6A$ methylation patterns varies at different brain regions with a dynamic involvement in neural development. Some recent studies show that miRNAs and RNA methylation in concert play an important role in post-transcriptional genetic regulation.

However, there is a lack of practical techniques that can analyze their correlation in post-transcriptional regulation with sufficient throughput and spatial information at a tissue-wide scale. The use of long priming probes in conventional FISH-based methods does not favor the profiling of small miRNAs. Although the nucleotide length of mRNAs with $m^6A$ methylation is sufficiently long for probe priming, additional biochemical analysis such as liquid chromatography is required to differentiate methylation levels within a pool of mRNAs. If there are more than one type of molecular targets from a population of individuals cells to be analyzed in-situ with sufficient spatial resolution, conventional techniques usually require mapping each type of molecular targets one-by-one, instead of a single cell level.

Current analytical methods based on sensing and quantifying fluorescent signals from different probes by conventional fluorescent microscopy are limited by the number of fluorescent channels, interference and crosstalk between different fluorescent channels, thereby limiting the number of applicable fluorophores and multiplexing throughput. Previously, FISH-based method and NanoString barcoding (a comparison between different conventional methods will be described hereinafter and summarized in Table 3) have been reported. FISH based fluorescence encoding requires super-resolution microscopy and involves serial rounds of hybridization, imaging and probe stripping, making it expensive, time-consuming and technically difficult for wider adoption. For NANOSTRING barcoding, the barcodes are prepared using a string of RNA particles coupled with fluorophores, which requires intricate sequence design and synthesis processes. In an assay, the reporter barcodes also need to be stretched by an electric field before imaging, further limiting its usage for in situ analysis. Though NANOSTRING has already been used in a spatial mRNA profiling, the implementation is of relatively low spatial resolution and slow profiling speed due to the sequential region by region cleaving process of the reporters.

Therefore, a need exists for a single cell multi-omic profiling approach including post-transcriptional regulation to capture spatial information of multiple molecular targets with subcellular resolution among a larger scale of cellular populations from a tissue-wide biopsy, and a new coding system for translating multi-spectral information from different fluorophores with overlapping emission wavelengths into corresponding codes containing specific spectral features, which at least diminishes, eliminates or overcomes the disadvantages, problems or challenges in the conventional techniques.

SUMMARY OF THE INVENTION

The present disclosure proposes a platform configured to massively capture intracellular molecular targets from a large population of cells in acute tissue slices and incorporating a robust molecular fishing system for targeting a wide variety of molecular targets at once. Captured or extracted intracellular molecular targets by the platform are analysed in-situ through an initial spatial registration and employing a subsequent barcoding strategy to enable a high-throughput multiplexing and quantification of molecular targets in different individual cells with respect to the spatial registration of extracted intracellular molecular targets by the platform. The proposed platform and strategy are sequencing-free, and capable of profiling multiple post-transcriptional molecular targets involved in genetic or epigenetic regulations in a single process run. Multi-spectral information obtained by different fluorescent channels from a specially-designed mixture of barcodes (or different ratios of fluorophores conjugated with different reporter probes) for hybridizing different intracellular molecules on the platform extracted from the tissue slice is digitalized and output to a network implementing one or more machine learning algorithms to analyse and extract the corresponding feature vector representing a specific type of molecular targets in order to quantify different types of molecular targets present in a population of cells and correlate the quantitative result to their spatial distribution across the tissue, in order to obtain a post-transcriptional profile of multiple molecular targets in a target tissue.

Accordingly, in a first aspect of the present invention, there is provided a molecular fishing system comprising an array of nanoprobes (or a plurality of vertically-aligned nanoneedles), where each of the nanoprobes (or nanoneedles) is functionalized with one or more molecular target fishing molecules for extracting molecular targets via intracellular biopsy, i.e., interfacing with a superficial layer of cells in a freshly prepared tissue slice.

In certain embodiments, the array of nanoprobes is made of silicon.

In other embodiments, the array of nanoprobes can be made of a material with sufficient mechanical strength to enable puncture of the nanoprobes into the tissue sample to a subcellular level.

In certain embodiments, the one or more molecular target fishing molecules include nucleic acids, proteins, antibodies, or any combination thereof.

In certain embodiments, the nucleic acids being the one or more molecular target fishing molecules are DNA or RNA molecules, or a combination thereof.

In certain embodiments, the DNA or RNA molecules being the molecular target fishing molecules include oligo (dT) primers and antisense oligonucleotides In certain embodiments, the molecular target fishing molecules are selected from p19 siRNA binding proteins for targeting microRNAs (miRNAs).

In certain embodiments, the molecular target fishing molecules are selected from anti-N6-methyladenosine ($m^6A$) antibody for targeting N6-methyladenosine messenger RNAs ($m^6A$ mRNAs).

In certain embodiments, other antibodies selected as the molecular target fishing molecules are for targeting proteins and other methylated DNAs or mRNAs.

In certain embodiments, the nanoprobes are initially amino-functionalized prior to cross-linking with the one or more molecular target fishing molecules.

In certain embodiments, each of the nanoprobes is configured to have a high height-to-base width aspect ratio.

In certain embodiments, each of the nanoprobes has substantially identical height, base width, and spacing with the other nanoprobe on the base of the array.

In certain embodiments, each of the nanoprobes has an average base width from 200 nm to 500 μm.

In certain embodiments, each of the nanoprobes has an average height from 2 μm to 200 mm.

In certain embodiments, between each pair of the nanoprobes there is an average spacing distance from 5 μm to 500 μm.

In an exemplary embodiment, the amino-functionalized nanoprobes are subsequently biotinylated followed by labeling with streptavidin conjugated fluorescent dye, prior to cross-linking with the one or more molecular target fishing molecules.

In a second aspect of the present invention, there is provided a method of mapping spatial distribution and expression of multiple molecular targets with individual cells within a two-dimensional tissue boundary. The method includes:

- contacting the array of nanoprobes described in the first aspect or according to certain embodiments described herein with a surface of a tissue sample at an interface where the one or more molecular target fishing molecules and the crosslinked fluorescent dyes on the nanoprobes will be in contact with a superficial layer of the tissue;
- extracting the molecular targets by the one or more molecular target fishing molecules from the tissue;
- exposing the other surface of the tissue sample to an imprint irradiation to imprint an outline of the tissue on the array; and
- removing the tissue sample from the array and subject the array to fluorescent imaging and subsequent barcoding.

In certain embodiments, the fluorescent dyes can be selected from any fluorescent dyes capable to emit light signals within a detectable range of the applicable microscopy but outside the spectrum of the imprint irradiation.

In certain embodiments, the fluorescent dyes have excitation and emission wavelengths from about 579 to 603 nm.

In certain embodiments, a crosslinker used to crosslink between the fluorescent dyes and the nanoprobes is UV cleavable.

In certain embodiments, a pixelated fluorescent pattern corresponding to the presence of the streptavidin conjugated fluorescent dyes on the nanoprobes covered by the tissue sample is obtained during the exposure to the irradiation.

In certain embodiments, after contacting the array of nanoprobes with the surface of the tissue sample at the interface where the one or more molecular target fishing molecules and the crosslinked fluorescent dyes on the nanoprobes will be in contact with a superficial layer of the tissue, a pressure is applied to the nanoprobes towards the tissue sample in order to puncture the nanoprobes into the superficial layer of the tissue for the subsequent extraction.

In certain embodiments, the pressure applied to the nanoprobes towards the tissue sample is by centrifugation of both the array of nanoprobes and the tissue sample held in a container.

In certain embodiments, the imprint irradiation for imprinting the outline of the tissue on the array is UV irradiation.

In certain embodiments, an image of the tissue and relative position of the nanoprobes is captured as a spatial registration of certain cell types in the tissue associated with the nanoprobes prior to the removal of the tissue sample from the array.

In certain embodiments, certain cell types in the tissue slice are labelled by immunostaining with specific markers.

In certain embodiments, the subsequent barcoding is performed by subjecting the array of nanoprobes to a plurality of reporter sequences complementary to the molecular targets extracted by the nanoprobes, where the corresponding reporter sequence is associated with a pre-determined mix ratio of multiple labelling agents for spectral analysis.

In a third aspect of the present invention, a spectrum barcoding system for profiling different molecular targets associated with post-transcriptional regulation mechanisms in individual cells of a tissue sample, in which the system includes a plurality of different sets of in-situ hybridization particles, and each set of in-situ hybridization particles is associated with a guiding probe and a plurality of labelling agents at a pre-determined mix ratio corresponding to a specific molecular target.

In certain embodiments, the in-situ hybridization particles are modified with a specific functional group to crosslink with the labelling agent.

In certain embodiments, the specific functional group is selected from amino group, hydroxyl group, carboxyl group, N-hydroxyl succinimide group, or sulfhydryl group.

In other embodiments, the in-situ hybridization particles can be modified by electrostatic adhesion or selected from porous particles for association with or absorption of different labelling agents.

In certain embodiments, the in-situ hybridization particles are in different shapes including spherical, nanoroad, nanowire, and star.

In certain embodiments, each of the in-situ hybridization particles has an average size of about 1 nm to about 1 cm.

In certain embodiments, the in-situ hybridization particles are beads in nano scale (or nanobeads).

In certain embodiments, the in-situ hybridization particles are made of one or more of magnetic material, inorganic material and a polymer, which include, but not limited to, $Fe_2O_3$, $Fe_3O_4$, silicon, silicon oxide, gold, silver, AlOOH, polystyrene, polyvinyl chloride, or any combination thereof.

In certain embodiments, the in-situ hybridization particles are magnetic beads.

In certain embodiments, the labelling agents have excitation and emission wavelengths from 300 nm to 800 nm.

In certain embodiments, the labelling agents are fluorophores.

Other than fluorophores, the labelling agents can be one or more of quantum dot, upconversion materials, fluorescent molecules and proteins conjugated with the in-situ hybridization particles according to other embodiments.

In certain embodiments, each combination of in-situ hybridization particles includes from at least 1 to 50 different types of labelling agents.

In certain embodiments, the pre-determined mix ratio of each type of labelling agent to the other type(s) in the same combination of in-situ hybridization particles is 1:1-99.

In other words, the mix ratio of each labelling agent is from 1/2 to 1/100 in the same combination of in-situ hybridization particles.

In certain embodiments, the guiding probe includes a nucleotide sequence or amino acid sequence complementary to a specific sequence of the molecular target, or antibodies, or any combination thereof.

In certain embodiments, the nucleotide sequence of the guiding probe is antisense oligoes to a DNA or RNA sequence of the molecular target.

In certain embodiments, the guiding probe is functionalized with one of biotin, amino group, hydroxyl group, carboxyl group, N-hydroxy succinimide group and sulfhydryl group.

In certain embodiments, the functionalized guiding probe is associated with the corresponding in-situ hybridization particle.

In some other embodiments, the guiding probe is a protein-RNA complex that is capable of recognizing a single base of the molecular target.

In certain embodiments, the in-situ hybridization particles can be further functionalized with one or more functional elements including plasmid, siRNA, drug, or a complex of sgRNA associated with any of Cas9, Cas12, and Cas13 proteins.

In certain embodiments, after a first round of in-situ hybridization particles contacts with the molecular targets on the nanoprobes, an emission pattern/spectrum from the corresponding labelling agent of the first round of in-situ hybridization particles associated with the array of nanoprobes is captured by all applicable channels of a multi-channel microscope, followed by cleavage of the guiding probe associated with the first round of the in-situ hybridization particles, and then the nanoprobes are exposed to a second or subsequent round of in-situ hybridization particles for capturing a second or subsequent emission pattern/spectrum from their respective labelling agent by the same applicable channels of the multi-channel microscope before the respective guiding probe being cleaved.

In certain embodiments, the number of applicable channels of the multi-channel microscope is at least 4.

In certain embodiments, the multi-channel microscope includes confocal microscope and other fluorescence detection device.

In a fourth aspect of the present invention, a spectral digitization method is provided to encode at least two conditions/statuses of each emission pattern/spectrum captured by each of the applicable channels of the multi-channel microscopy in the spectrum barcoding system of the present invention, where the method includes encoding the at least two conditions of the emission spectrum detected by each applicable channel with at least two numbers.

In certain embodiment, the two numbers (binary strategy) employed to encode two different conditions are "1" and "0" to represent the presence and absence of an emission spectrum in an individual cell, respectively.

In certain embodiments, the total number of spectrum barcodes under a binary mixing strategy is determined by $N\times(2^C-1)$, where C denotes the number of applicable channels for encoding; N denotes the number of hybridization/visualization round, and where the barcode "0000" is not used when the number of applicable channels is 4 and only one round of in-situ hybridization is performed.

In other embodiments, a trinary mixing strategy is employed to encode for three different conditions in case where the throughput is further enhanced by increasing a mix ratio of multiple labelling agents, wherein different brightness levels (or intensity levels) of an emission spectrum of a labelling agent detectable by the applicable channel of the microscopy are encoded as "0", "1", and "2", respectively.

In the embodiments that the mix ratio of multiple labelling agents is increased, the throughput of the spectrum barcoding system in each single process run can be determined by the following equation:

$$N \times (R_{step}^{C} - 1)$$

where $R_{step}$ denotes the ratio step number; C denotes the number of applicable channels, and N denotes the number of hybridization/visualization rounds.

In certain embodiments, emission spectra captured by the respective applicable channel of the multi-channel microscope after said encoding are further processed by extracting features from region of interests (ROIs) followed by optimization before barcode feature vectors are generated.

In certain embodiments, the tissue sample is stained with a cell-specific labelling agent and fluorescent images thereof are captured for image segmentation by adaptive binarization before feature extraction from the ROIs.

In certain embodiments, the generated barcode feature vectors are decoded by machine learning based models or algorithms, including but not limited to, linear regression, logistic regression, decision tree, SVM, Bayes and KNN, or advanced deep-learning algorithms, such as Convolutional Neural Networks (CNNs), Long Short Term Memory Networks (LSTMs), Recurrent Neural Networks (RNNs).

Other aspects of the present invention include a kit for multiplex detection of molecular targets including the in-situ hybridization particles described herein with a pre-determined mix ratio of labelling agents having different or similar (overlapping) excitation and emission spectra associated with one or more guiding probes for different genotypes or species of molecular targets, together with an implementation of the digitalized spectrum barcoding strategy described herein such that microscopy with a limited number of channels/limited resolution or labelling agents having high crosstalk with each other can still achieve a significantly high throughput due to the encoding and decoding mechanisms employed in the present invention.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The patent or application file contains at least one drawing executed in color. Copies of this patent or patent application publication with color drawing(s) will be provided by the Office upon request and payment of the necessary fee.

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

Figure 1:
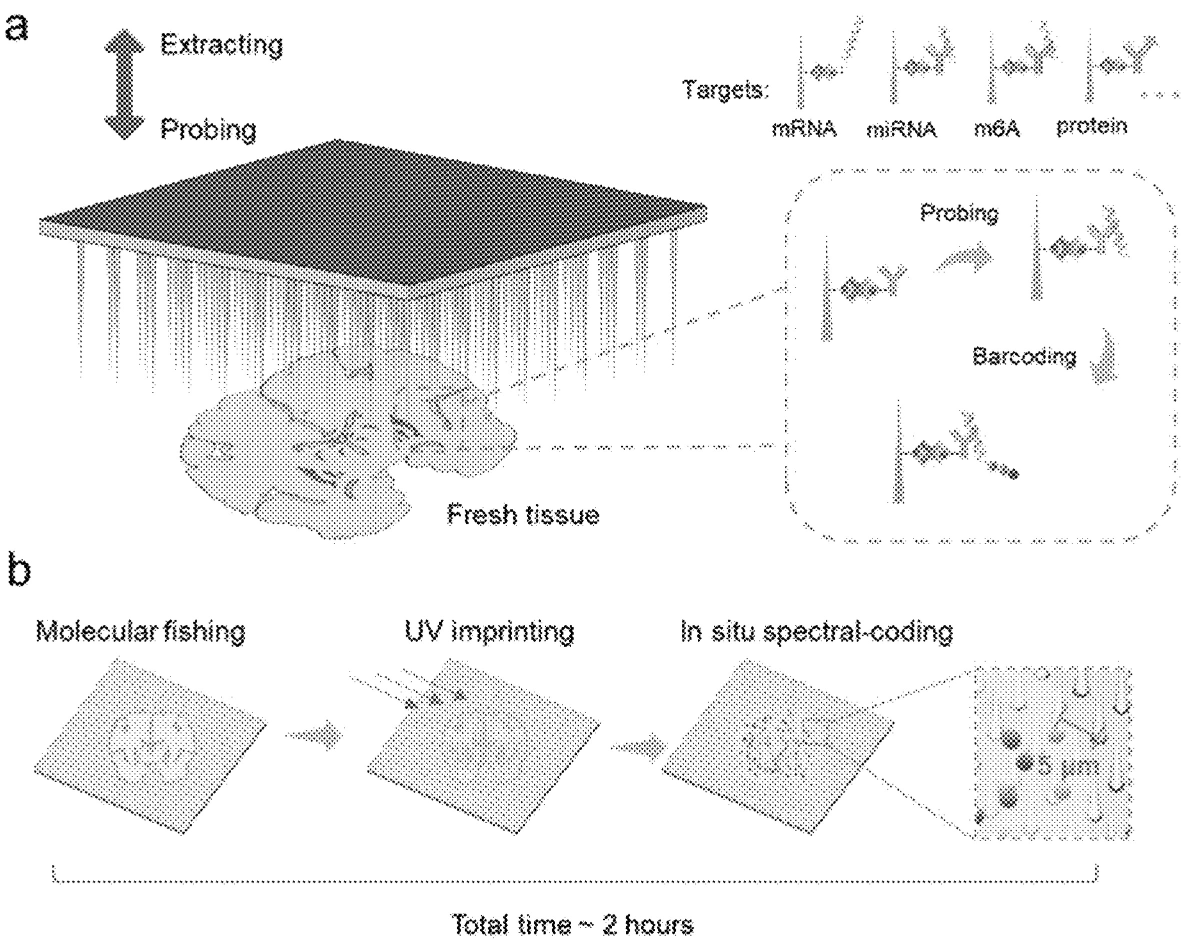
FIG. 1 schematically depicts spatial profiling of various intracellular molecular targets: (a) extracting and probing various molecular targets from fresh tissue by nanoprobe array (or biochip) according to certain embodiments; (b) major schemes of the present invention, namely molecular fishing, UV imprinting and in-situ spectral-coding schemes.

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Value in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

In the methods of preparation or using the system, device, apparatus, or alike described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

The present invention provides a platform for extracting molecular targets in a tissue-wide scale and a high throughput method to locate and map the expression pattern with different sections of the tissue sample while a proposed digitized spectrum barcoding strategy enables multiplexing in a limited number of visualization channels by using a set of different mix ratio of fluorophores-labelled particles and taking their signature spectral pattern to quantify copies of a specific molecular target based on certain machine learning based algorithms. A spatial post-transcriptome analysis of both miRNAs and methylated mRNAs with single cell resolution across a millimeter to centimeter brain tissue slice is enabled. By the present platform, the molecular information is sampled and preserved by individual nanoprobes, which are registered to thousands of cells in an acute tissue slice after the initial cellular contact for intracellular molecular fishing. To achieve such spatial mapping, a UV imprinting scheme is proposed to acquire a pixelated tissue morphology feature on the array of nanoprobes with a larger footprint than the tissue. Under the proposed UV imprinting scheme, as all the nanoprobes are labeled with a photocleavable fluorescent dye, a brief UV exposure will be sufficient to cleave off the dyes on nanoprobes that are not covered (unmasked) by the tissue sample, thus to generate a contrasted fluorescent pattern of the tissue outline on the biochip, providing a reference framework for spatial registration to subsequent tissue images to be acquired by immunostaining and optical microscopy. Unlike the conventional spatial indexing methods that typically involve molecular sampling with tremendous efforts in spatial control, the proposed UV imprinting scheme facilitates spatial encoding which is easy to implement and does not require any special equipment, such as robotic sampler or microfluidic chamber, making it extremely cost-effective. Together with a custom-made imaging processing algorithm, each nanoprobe can be traced back to individual cells at subcellular resolution to reveal the post-transcriptional profiles across a whole centimeter tissue sample.

In certain embodiment, the platform incorporates a biochip with an array of vertically aligned nanoprobes to effectively extract intracellular molecules (miRNAs, $m^6A$-mRNAs) for downstream analysis in the coordinates of the large-scale of cells within a tissue slice.

The present disclosure also proposes a digitalized spectrum barcoding approach to achieve multiplexing throughput in a relatively limited number of fluorescent channels or absent super-resolution microscopy. The digitalized spectrum barcoding approach relies on a "rainbow" fluorescence composition (i.e., a mixture of different fluorophores or luminescent labelling agents) and a machine learning based spectrum decoding method for functional differentiation of multiple molecular targets in a single cell. The simplest spectrum digitalization is based on a binary mixing strategy, e.g., to assign the presence and absence of fluorescence signal at each channel from the nanoprobes after each round of in-situ hybridization with the corresponding combination of nanobeads with a pre-determined mix ratio of multiple fluorophores as "1" and "0", respectively. To enhance the multiplexing, multi-round visualization strategy by DNase-assisted removal of spectrum barcodes at each round of in-situ hybridization is proposed. Theoretically, the encoding pool can be further expanded if the rainbow fluorescence dyes mix ratio changes from the current binary format and adopts a step-wise ratio for different fluorophores, i.e., the number of available codes will be $N\times(R_{step}^{C}-1)$, where $R_{step}$ indicates the ratio step number, C indicates the fluorophore channels number, and N indicates the rounds of visualization cycles. For example, with a larger mix ratio number, using a trinary mixing strategy, with '0', '1' and '2' for three different conditions in each channel, there will surely be higher throughput. Therefore, under the trinary mixing strategy with 7 different fluorophores, the multiplexing throughput can be significantly increased to over 10,000 by 5 rounds of visualization.

Turning to FIG. 1, an orderly array of silicon nanoprobes was utilized to disrupt cell membrane for access to intracellular domain and to extract targets of interest from individual cells. Specifically for acute tissue samples, all the cells under the coverage of the biochip are simultaneously examined with a single operation. Unlike conventional spatial transcriptomics technologies, where the tissue samples typically require extensive pre-treatment before genetic or transcriptional analysis, the present invention directly applies on freshly prepared acute tissue slices, making it a lot more convenient and cost-effective. In certain embodiments, the nanoprobes are fabricated as a square array of vertical cylinders. In certain embodiments, the nanoprobe's base width, height and a spacing between two adjacent nanoprobes on the square array are about 800 nm, 7 m, and 5 m, respectively. Details of fabrication process and characterization of the nanoprobes as a square array of vertical cylinders will be provided in certain examples described herein and depicted in FIGS. 2A-2D and 3.

Depending on the targets to be extracted/isolated, different 'bait' molecules (or molecular target fishing molecules) are functionalized on the nanoprobes for molecular extraction/isolation (or called "molecular fishing"). For example, for miRNAs extraction, p19 protein is used; for extracting RNAs with $m^6A$ modifications, specific antibodies are used. Other possible examples of "bait" molecules include poly(T) sequences for extracting mRNAs, different antibodies for extracting signaling proteins or methylated RNAs, RNA-binding proteins (RBPs) for extracting interactive translational regulation factors, etc. It should be understood that more than one "bait" molecules can be functionalized on each of the nanoprobes to enable extraction/isolation of multiple molecular targets from each individual cell of the tissue sample simultaneously.

Figure 4A:
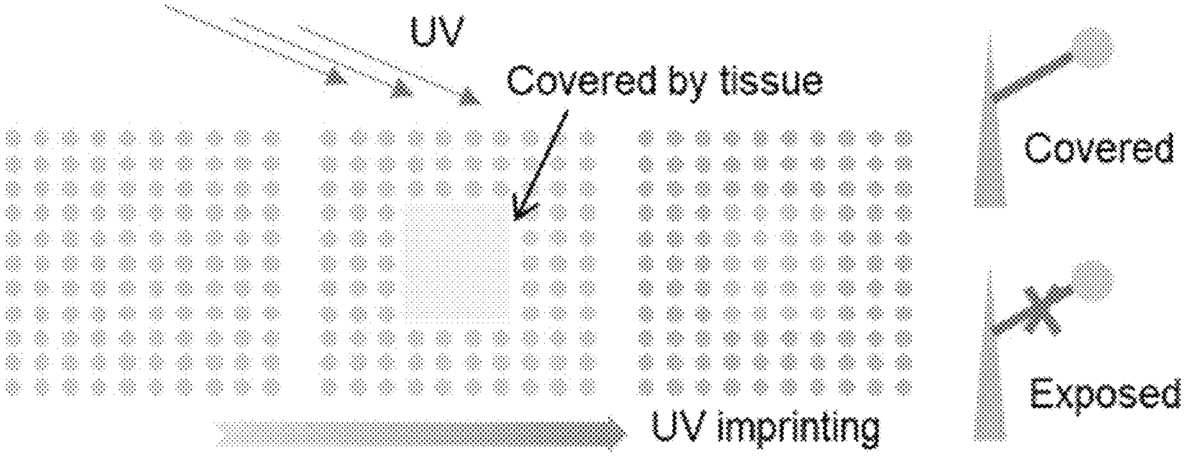
FIG. 4A schematically depicts UV imprinting scheme according to certain embodiments of the present invention.
Figure 4B:
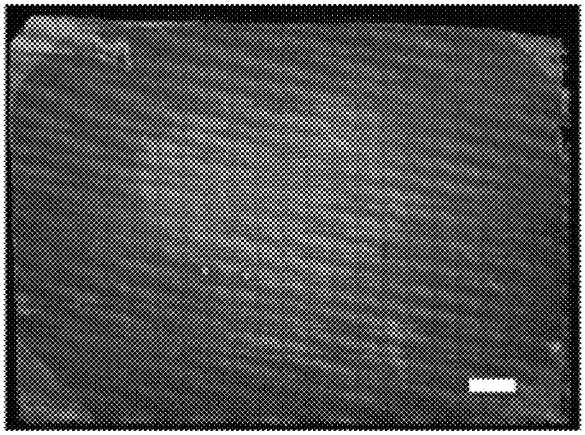
FIG. 4B shows a fluorescence image of a tissue sample covering the nanoprobe array according to the UV imprinting scheme depicted in FIG. 4A.
Figure 4C:
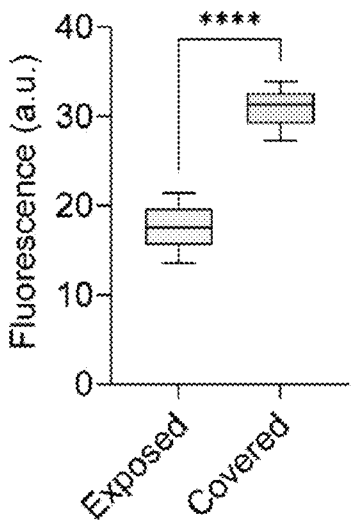
FIG. 4C shows the difference in fluorescence from the nanoprobe array with or without tissue coverage under a UV-induced cleavage of the fluorescence labels from the nanoprobes.
Figure 4D:
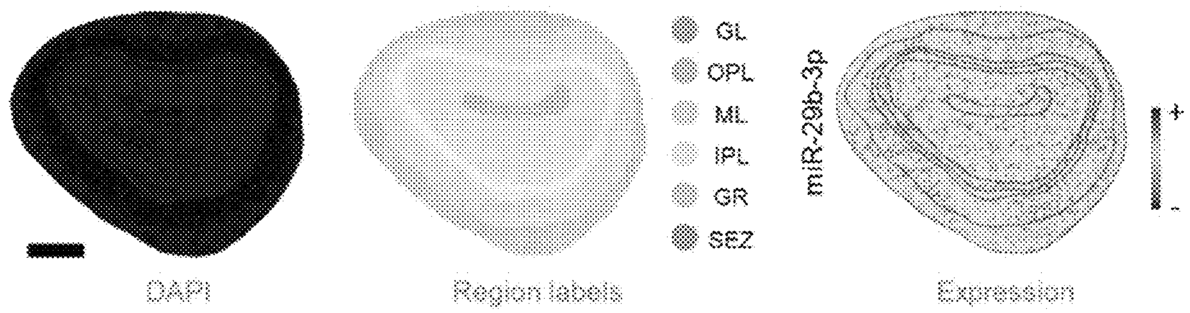
FIG. 4D shows an example of spatial profiling of miRNA targets in an acute olfactory bulb (OB) according to certain embodiments of the present invention: left panel: nuclear staining by DAPI; middle panel: labels of different regions; right panel: expression profile of a specific miRNA target, miR-29b-3p, across the OB slice; GL: glomerular layer; OPL: outer plexiform layer; ML: mitral layer; IPL: inner plexiform layer; GR: granule layer; SEZ: subependymal zone; scale bar: 400 m.

In the context of using the present nanoprobe array in epi-transcriptome analysis at single cell level, it is important to map the nanoprobes in the coordinates associated with a large number of cells with microscale resolution. In certain embodiments, a UV imprinting strategy is employed by labelling the nanoprobes with a fluorescence dye, e.g., ALEXA FLUOR 568, or AF-568 by a photo-cleavable crosslinker. When a piece of tissue slice (smaller than the array) is interfaced with the nanoprobes for "molecular fishing", a brief UV irradiation (e.g., at 365 nm, ~5 mw/$cm^2$) is applied, which energy level is just enough to cleave the photo-cleavable crosslinker in order to remove the fluorescence labels from the nanoprobes under a direct UV exposure, while the part covered by the tissue (masked region) remains unaffected (FIG. 4A), with a fluorescence image thereof showing a pixelated morphology and boundary features of a tissue slice on the nanoprobes under a fluorescent microscope (FIG. 4B). There is still a low fluorescence detected from the exposed region (unmasked by the tissue slice where the AF-568 are cleaved), which may be due to some background noise (FIG. 4C). The pixelated pattern and boundary features of the tissue slice will be used to register the nanoprobes with individual cells at subsequent analytical stages. FIG. 4D shows an example of identifying miRNA expression from an OB acute slice by using a molecular target fishing molecule specific to miR-29b-3p (the probe sequence) to functionalize the nanoprobes and map the expression thereof with the pixelated pattern of the nanoprobes in different OB tissue sub-regions.

Figure 3:
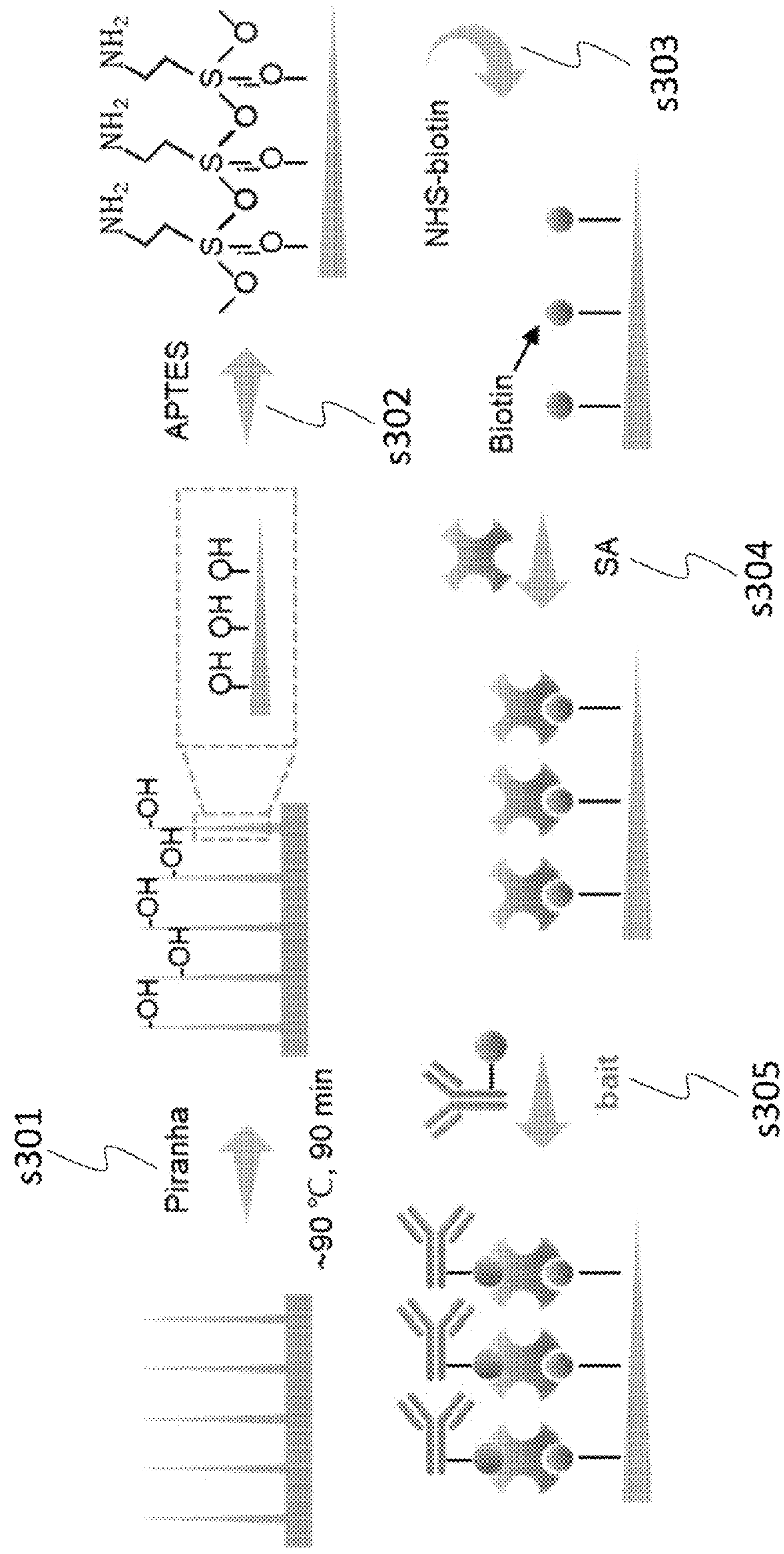
FIG. 3 schematically depicts functionalization scheme of nanoprobes according to certain embodiments of present invention.
Figure 5A:
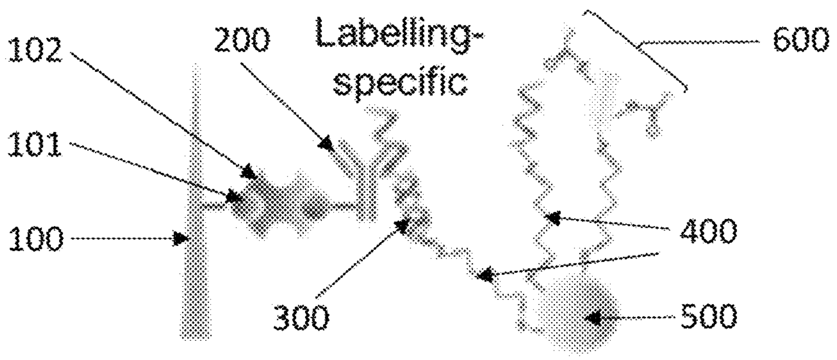
FIG. 5A schematically depicts molecular extraction by molecular target fishing molecules (baits) on nanoprobes and probing by corresponding guiding probe (an antisense oligo) on in-situ hybridization particles associated with different ratio of fluorophores (upper panel); and a multi-round hybridization scheme by using different combinations (batches) of the in-situ hybridization particles to hybridize with the extracted molecular targets on the nanoprobes to increase barcoding throughput (lower panel) according to different embodiments of the present invention.
Figure 5A:
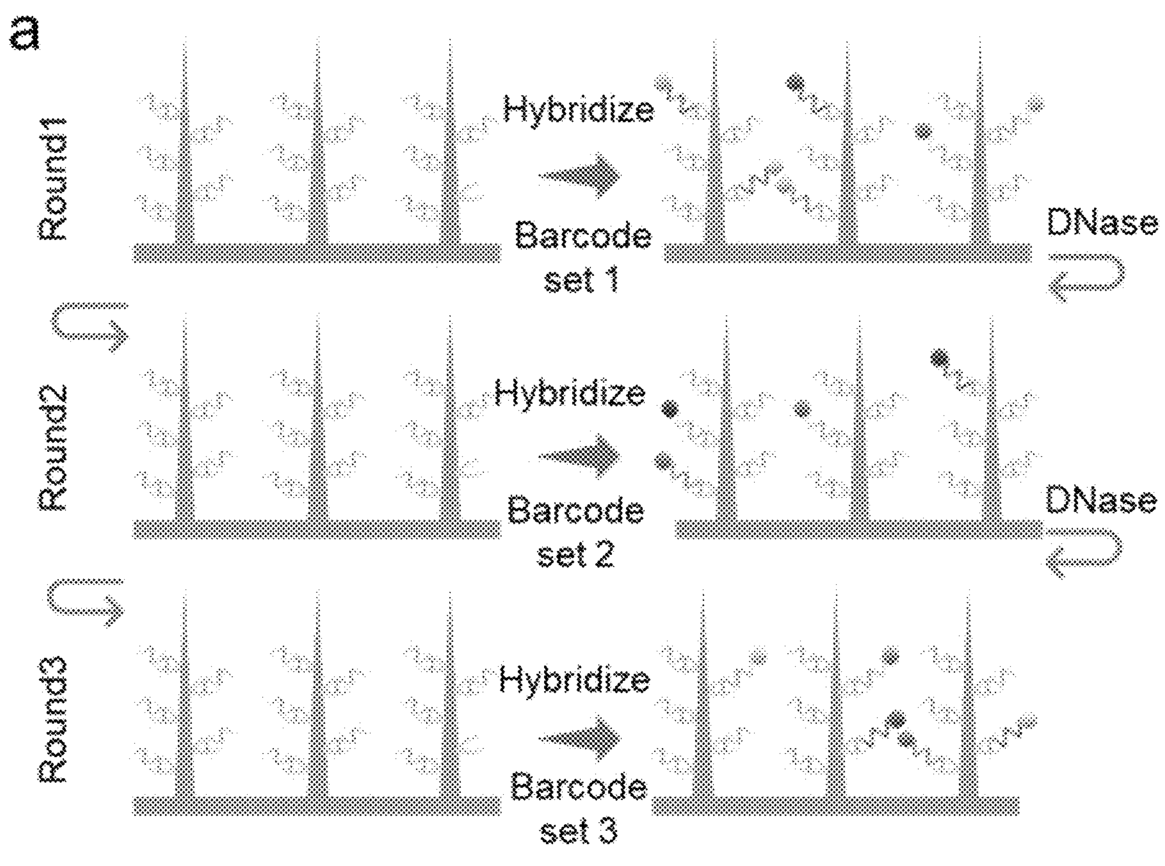

The upper panel of FIG. 5A depicts a preferred embodiment of the molecular fishing scheme used in the present invention to extract a molecular target and how the extracted molecular target is further visualized in a multiplexing throughput and single cell manner in the presence of a spectrum barcoding system. Each nanoprobe 100 is modified with a functional group. The nanoprobe can be made of silicon or other material with sufficient mechanical strength to enable insertion thereof into a tissue sample under an application of pressure. The functional group can be selected from amino group, hydroxyl group, carboxyl group, N-hydroxyl succinimide group, or sulfhydryl group. As shown in FIG. 3, the nanoprobes are first treated with piranha solution (s301), followed by treating with (3-aminopropyl)triethoxysilane (APTES) to functionalize the nanoprobes with amino functional group (s302). After activated by glutaraldehyde and biotinylated (s303), the nanoprobes are further conjugated with the bait molecules 200 (s305) to the biotin site 101 through a link by a streptavidin molecule 102 (s304), where the bait molecule is also biotinylated 101. After the bait molecules are conjugated, unlabelled biotin may be added to block the unreacted streptavidin sites.

When the molecular target is miRNAs, the bait molecules are selected from p19 siRNA binding proteins, whereas when the molecular target is $m^6A$ mRNAs, the bait molecules are selected from anti-N6-methyladenosine ($m^6A$) antibodies.

After the molecular fishing and UV imprinting, the extracted molecular targets on the nanoprobes are further subject to spectrum barcoding in the presence of nanobeads 500 associated with a complementary guiding probe 400 for in-situ hybridization with a specific molecular target 300. Depending on the throughput and the number of applicable fluorescence channels of the spectral system, a certain number of fluorophores at a pre-determined mix ratio is prepared and conjugated with the nanoprobe-molecular target-nanobead complex such that each species of molecular targets has a unique spectrum barcode (or spectrum profile).

In certain embodiments, the guiding probe is a DNA sequence antisense to a specific nucleotide sequence on the molecular target, which is associated with certain number of fluorophores at a pre-determined mix ratio.

When four applicable channels are used, a mixture of fluorophores used to conjugate with the nanobeads through a functional group such as amino group before hybridization with the specific nucleotide sequence on the molecular target is prepared by mixing four different fluorophores having different or overlapping excitation and/or emission spectra with each other.

Figure 6A:
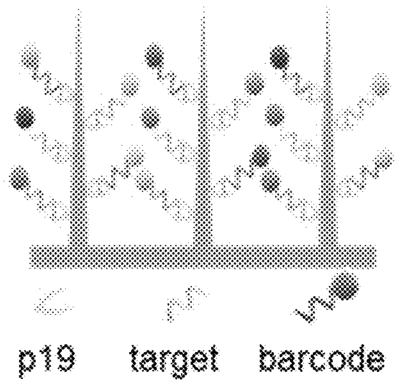
FIG. 6A schematically depicts the multiplexing strategy according to certain embodiment by using the in-situ hybridization particles (nanobeads) incorporated with multiple fluorescence labelling agents (rainbow fluorescence labelling) to encode different molecular targets on the nanoprobes; p19: p19 siRNA binding proteins being a molecular target fishing molecule (or bait); target: corresponding molecular target of p19 extracted from biopsy by the nanoprobes; barcodes: nanobeads conjugated with multiple fluorescence labelling agents.

In some working examples, AF-488, AF-514, AF-555, and AF-647 were mixed together at a pre-determined mix ratio. A mix ratio of each fluorophore to the rest of the fluorophores in the preparation may be 1/2, 1/3, 1/4, . . . up to 1/100. In most cases, the working excitation and emission spectra of the fluorophores are within a range of wavelengths from 300 nm to 800 nm. An example of using four different fluorophores to prepare the spectrum barcoding system for in-situ hybridization with the molecular targets on the nanoprobes is depicted in FIG. 6A.

Figure 5B:
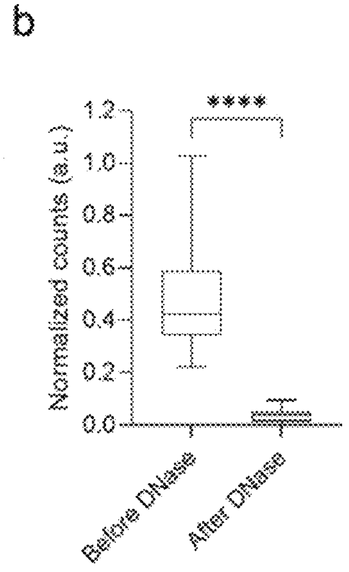
FIG. 5B shows the difference in in-situ hybridization particle counts before and after cleavage of the corresponding guiding probe by DNase in each round of in-situ hybridization according to the multi-round hybridization scheme depicted in FIG. 5A.

Referring to the lower panel in FIG. 5A, to increase the barcoding throughput of the spectrum barcoding system, a multi-round in-situ hybridization scheme is proposed, particularly useful for analyzing RNAs, where the DNA probes resulted from one round of hybridization can later be removed by a DNase treatment to further expand the analytical throughput by multiple rounds of probe hybridization towards more molecular targets. FIG. 5B provides the difference in nanobead counts before and after DNase cleavage at one round of the proposed multi-round in-situ hybridization scheme on a tissue sample.

Figure 6B:
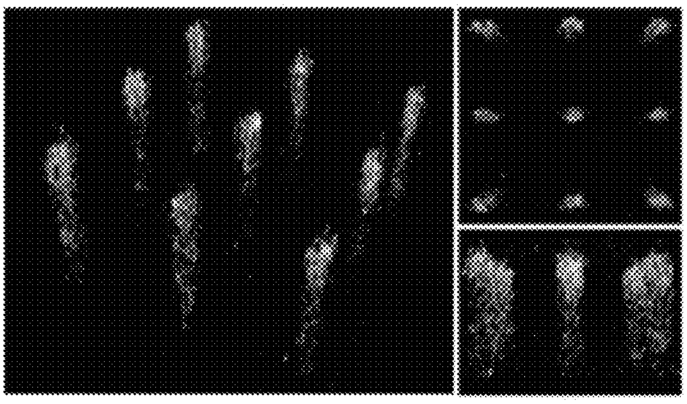
FIG. 6B shows digital images of different barcodes associated with extracted targets on the nanoprobes according to the strategy depicted in FIG. 6A from different three-dimensional views; scale bar: 5 μm.
Figure 6C:
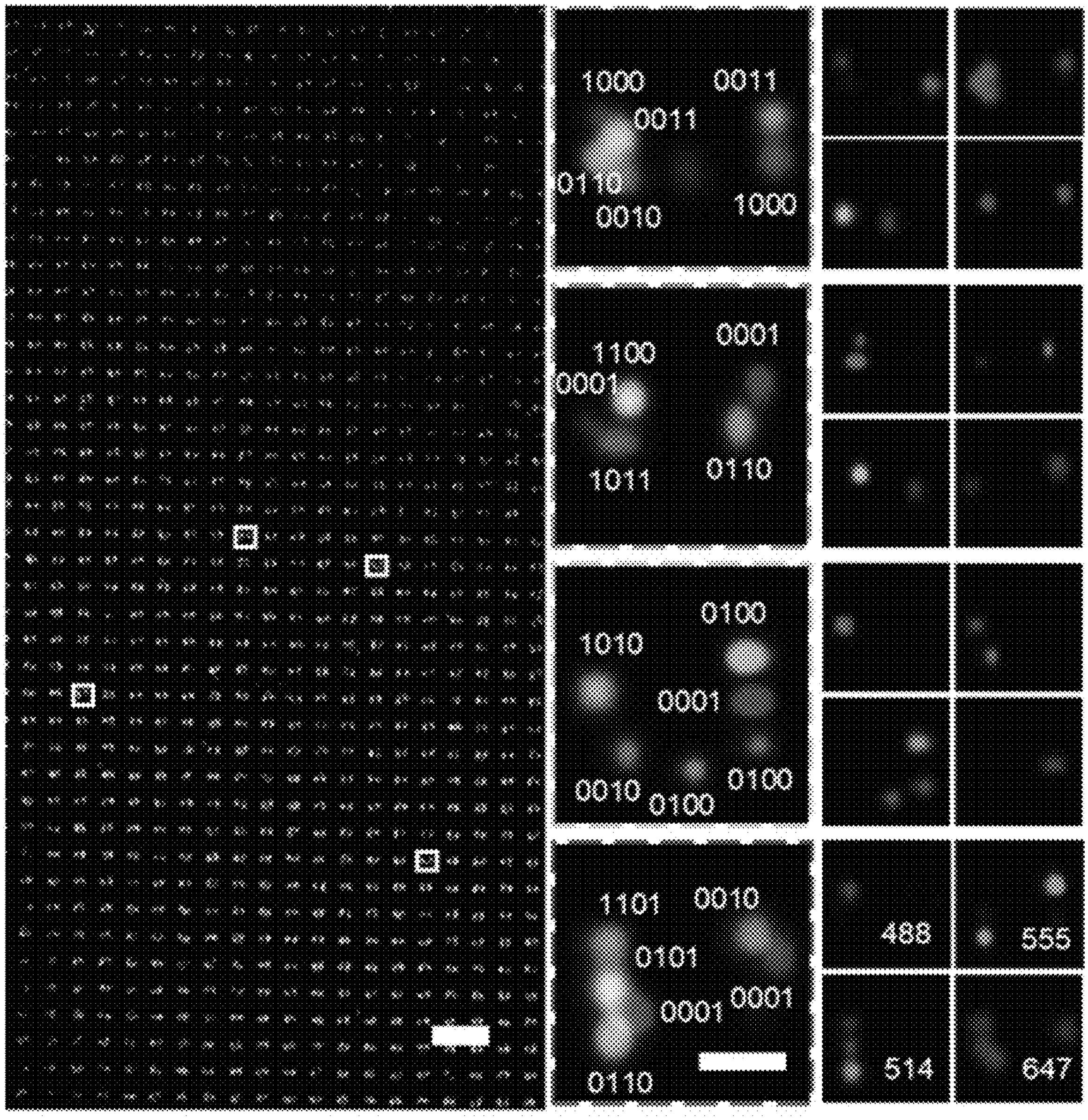
FIG. 6C shows a large-scale fluorescence image (left panel) of the nanoprobes probed by the nanobeads encoded with different spectra according to the strategy depicted in FIG. 6A including four fluorescence channels: ALEXA FLUOR (AF) 488 (in violet), AF 514 (in blue), AF 555 (in green) and AF 647 (in red); the boxed regions on the large-scale fluorescence images are magnified and shown in the middle column with label of their corresponding four-bit barcodes (excluding "0000"); individual fluorescence channels are split and shown on the right panel; scale bars: 10 μm (left panel), 500 nm (middle column).
Figure 6D:
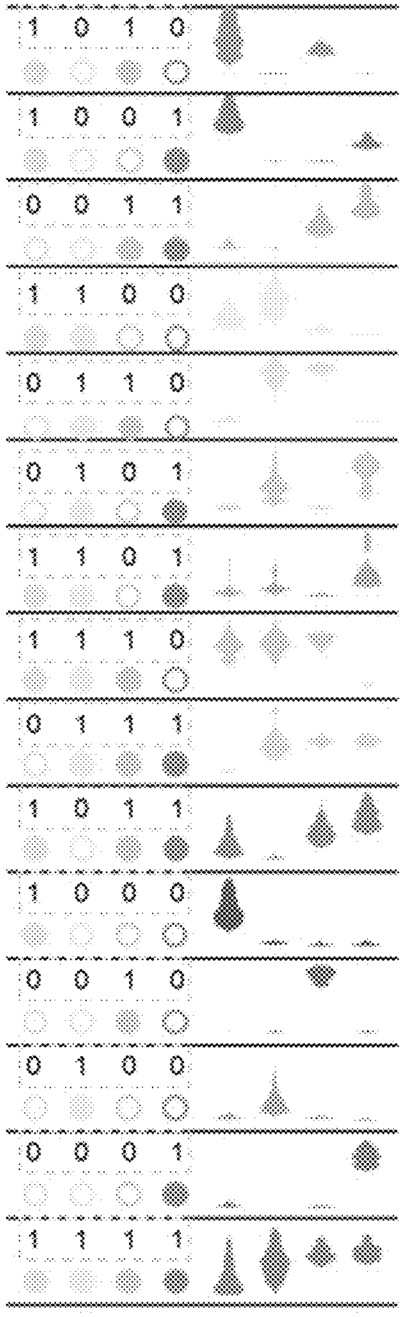
FIG. 6D shows violin plots of 15 barcodes generated from the readouts of four fluorescence channels excluding "0000" (left panel) and their spectral vectors (right panel); n>200.
Figure 6E:
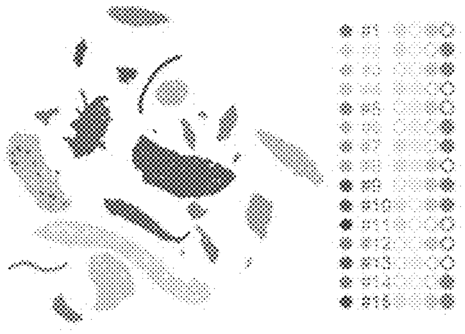
FIG. 6E shows well-separated clusters of 15 barcoded spectral vectors obtained from the plots in FIG. 6D and analyzed by Uniform Manifold Approximation and Projection (UMAP).
Figure 6F:
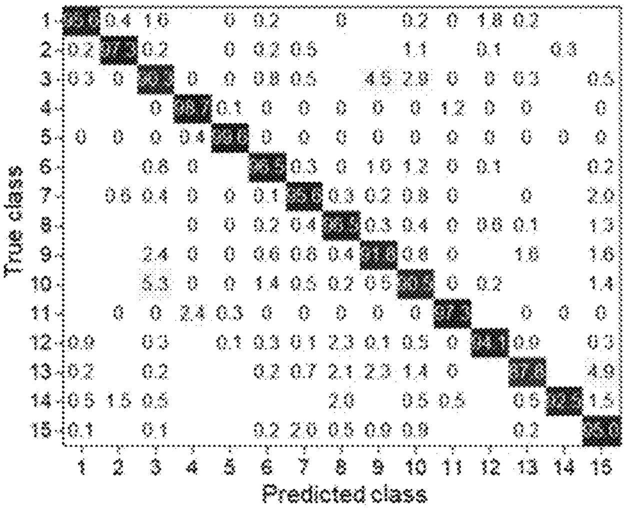
FIG. 6F shows a confusion matrix for classification accuracy of a machine learning algorithm for molecular multiplexing and decoding the 15 barcodes as in FIG. 6D according to certain embodiments of the present invention.
Figure 6G:
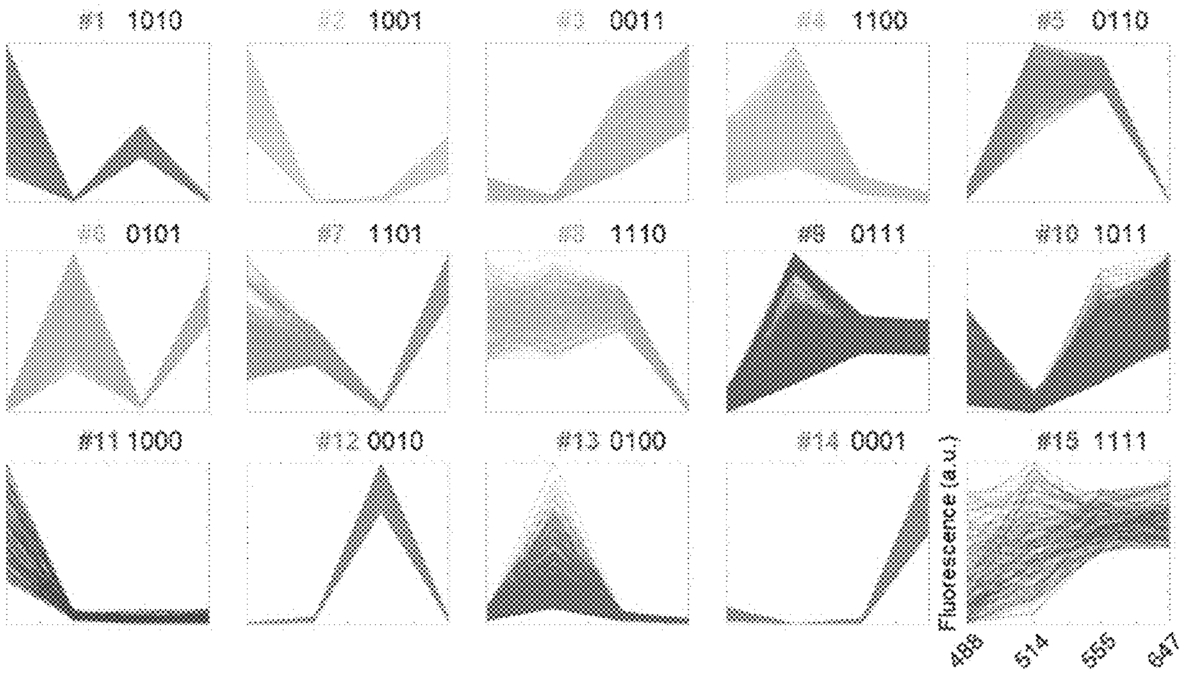
FIG. 6G shows feature distributions of 15 different barcodes in terms of their intensities at each fluorescence channel.
Figure 6H:
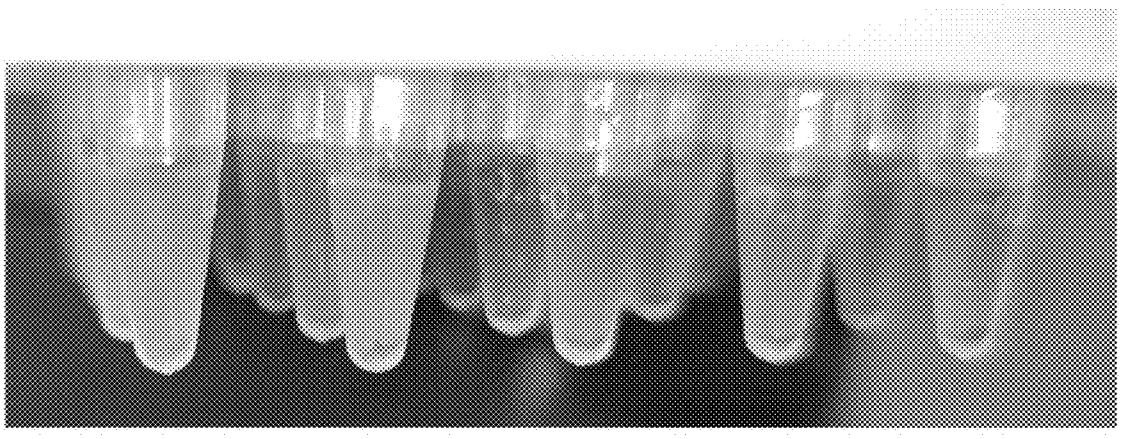
FIG. 6H shows an image of different nanobead mix with different nanobeads conjugated with different mix ratios of fluorophores.

Theoretically, by using a multi-channel spectral system for analysis could render the number of codes totaled from the equation $N\times(2^C-1)$, where C is the number of applicable fluorescent channels; N is the rounds of the hybridization analysis, and the barcode "0000" (representing blank or no fluorescence) is not used. In the example using a four-channel spectral system for capturing the fluorescence signals, the "rainbow" fluorescent beads can be encoded by 15 different spectral combinations. Different nanobead preparations having different mix ratio of fluorophores provide different visualization effects (an example prepared in vials with different colors is shown in FIG. 6H). A three-dimensional visualization of the rainbow fluorescent nanobeads on nanoprobes is shown in FIG. 6B, while FIG. 6C shows a pixelized pattern of nanoprobes overlaid with the fluorescence signal acquired from 4 spectral windows corresponding to the emission spectra of AF-488, AF-514, AF-555 and AF-647 fluorophores. In the binary encoded labelling, each bead is encoded as "1" or "0" for each spectral window of the four-channel spectral system. By use of a developed computational analysis such as Uniform Manifold Approximation and Projection (UMAP) protocol, digitized spectral vectors of all the beads as shown in FIG. 6D can be well separated, and graphically represented as in FIG. 6E.

Figure 19:
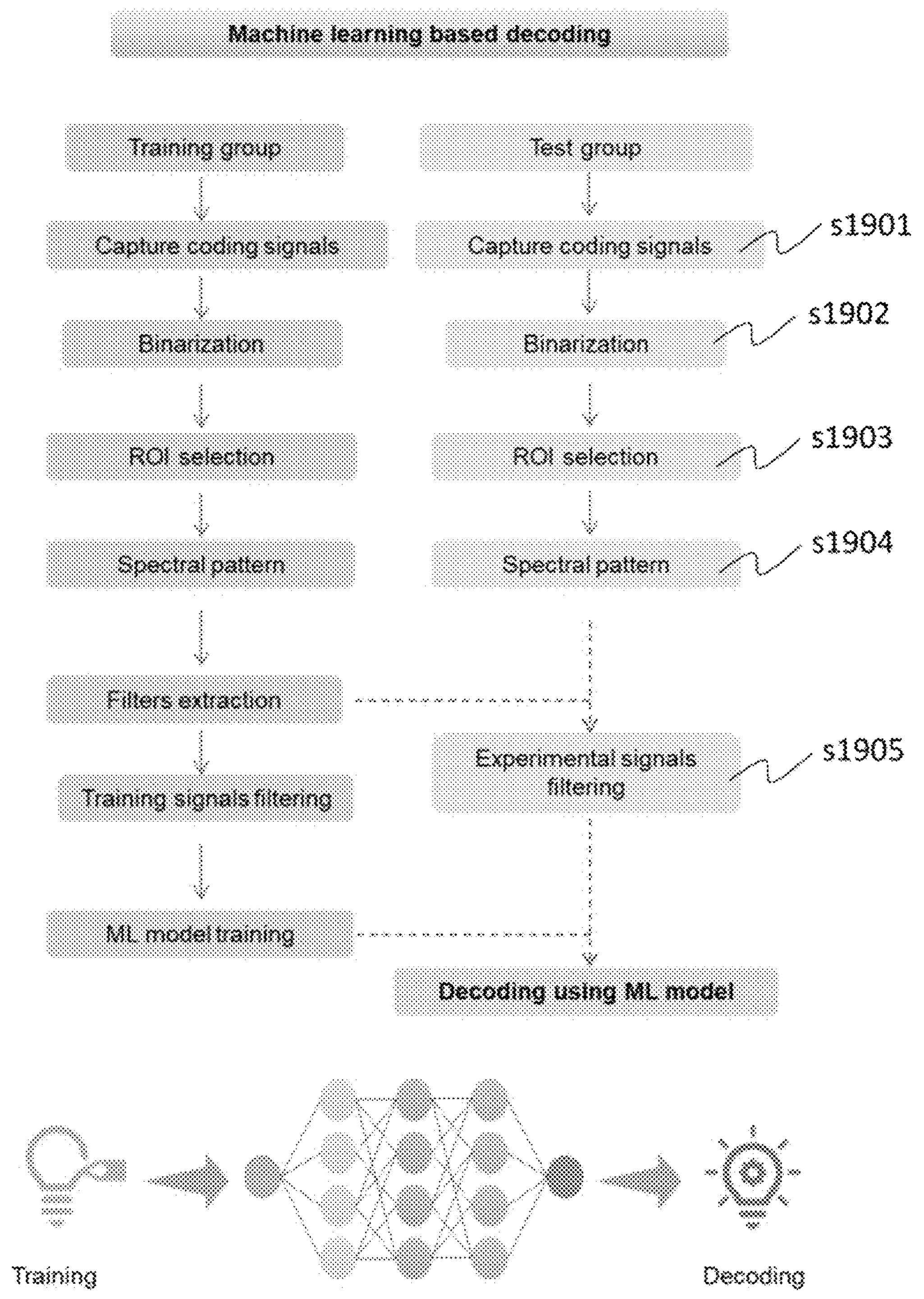
FIG. 19 shows a workflow with a schematic diagram for a proposed decoding scheme of spectrum barcodes by a machine learning based model according to certain embodiments of the present invention.

To overcome the interference by the variation of fluorescence intensities and a low level of background signal, especially in the "0" coded spectral window, a machine learning based algorithm is used to differentiate different digital spectral features from the 15 barcoded spectral vectors. FIG. 6F shows the classification accuracy for molecular multiplexing and decoding of 15 barcoded spectral vectors (FIG. 6G) using an exemplary machine learning based model as depicted in FIG. 19. By using the exemplary machine learning based model, an autonomous recognition of the digital spectrum barcodes with nearly 90% accuracy can be achieved.

Figure 15:
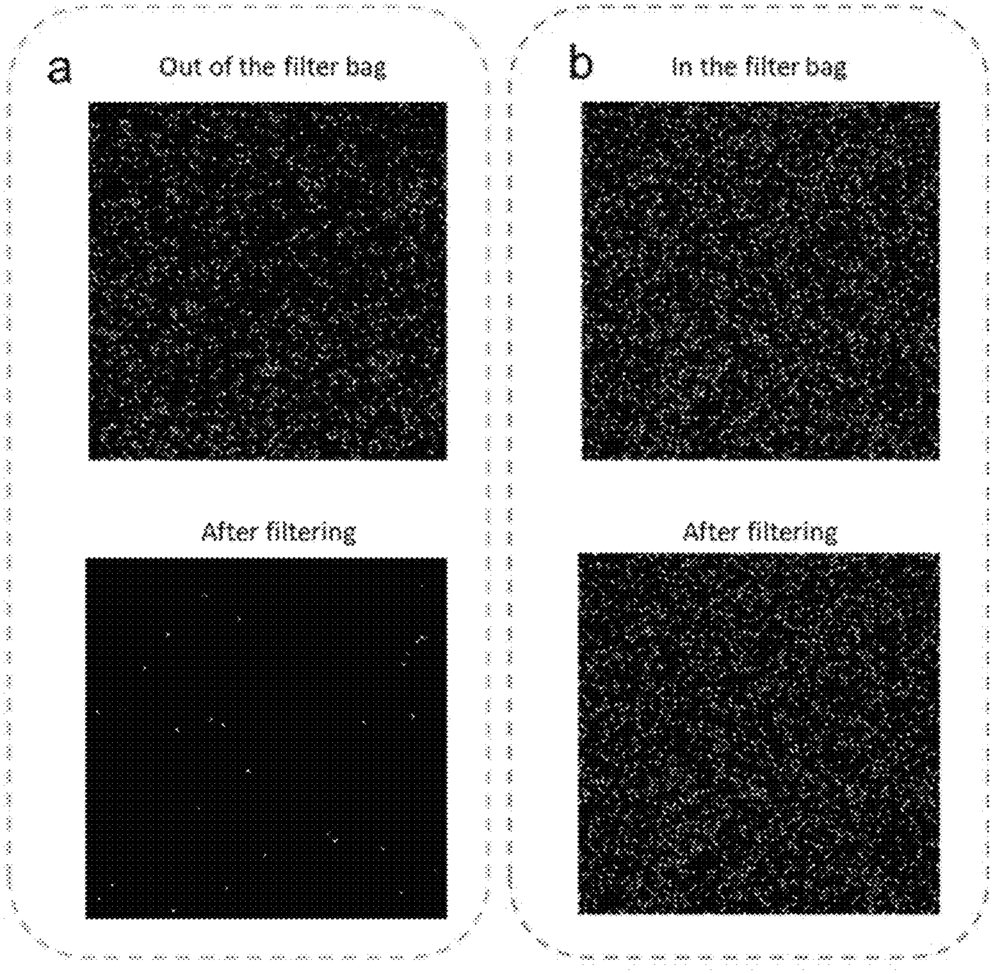
FIG. 15 shows a filter bag system for removing microscopic noises according to certain embodiments: (a) out of the filter bag before (upper panel) and after (lower panel) removal of barcodes; (b) within the filter bag where the barcodes are retained before (upper panel) and after (lower panel) removal of barcodes.
Figure 20:
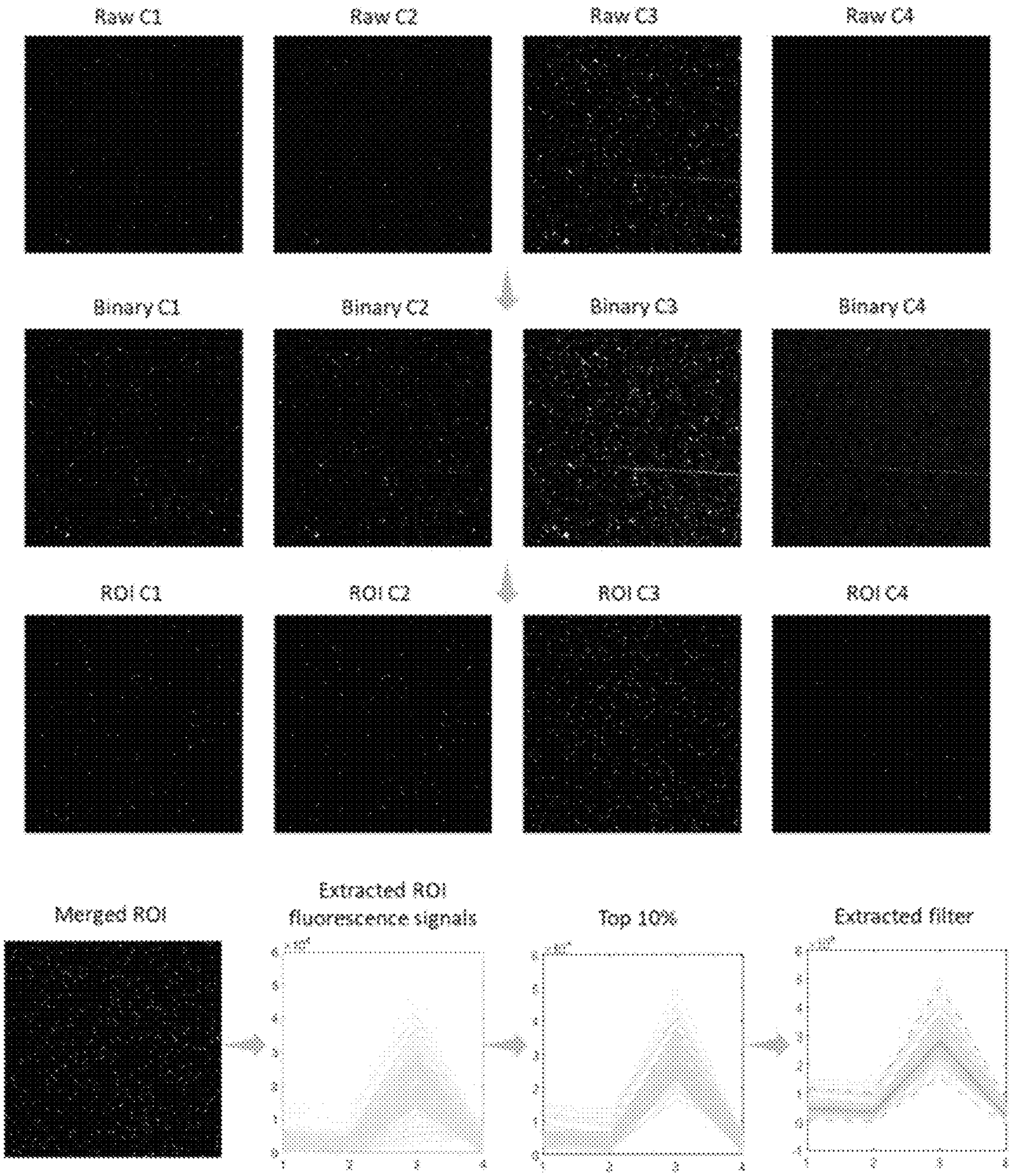
FIG. 20 shows image processing pipeline for ROI extraction and filtering based on the different fluorescence encoding.
Figure 21:
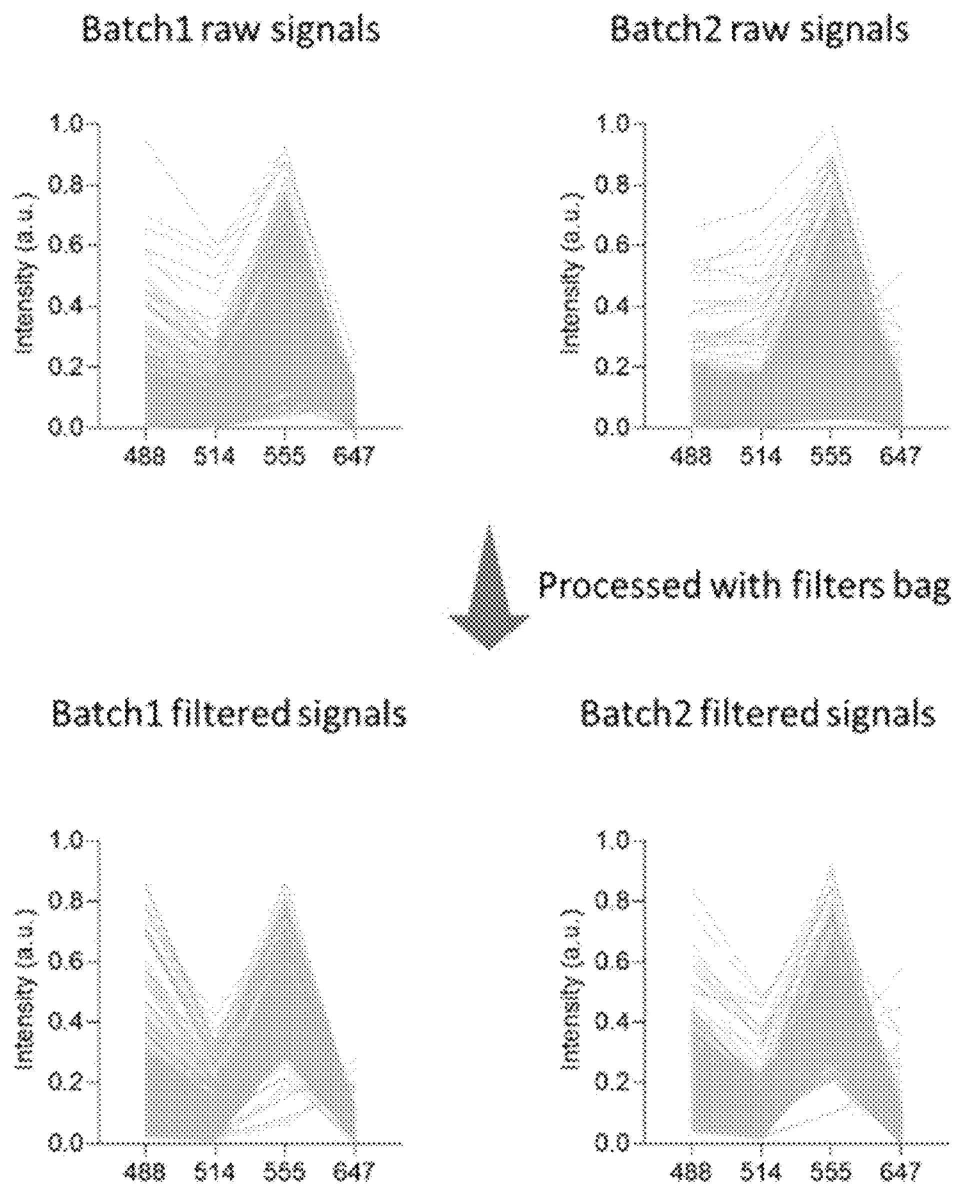
FIG. 21 an analysis of batch variation for nanobeads having the same barcode but being synthesized in different batches.

In some uncertain cases, that is, the nanobeads with ambiguous signal which does not carry a typical spectral feature or simply a noise resulted from microscopic imaging, a 'filtering' step (as illustrated in FIG. 20) is proposed to eliminate those variations or noises by using a physical filter bag to remove any unconjugated nanobeads from the nanoprobes out of the filter bag (FIGS. 15 and 21).

After the spectrum decoding based on the proposed machine learning based model, for each target, the number of nanobeads on individual nanoprobes are counted to indicate the copy number of the molecular targets (e.g. miRNA or mRNA), in order to quantity the corresponding post-transcriptional expression of different molecular targets in individual cells across the tissue sample.

Figure 7A:
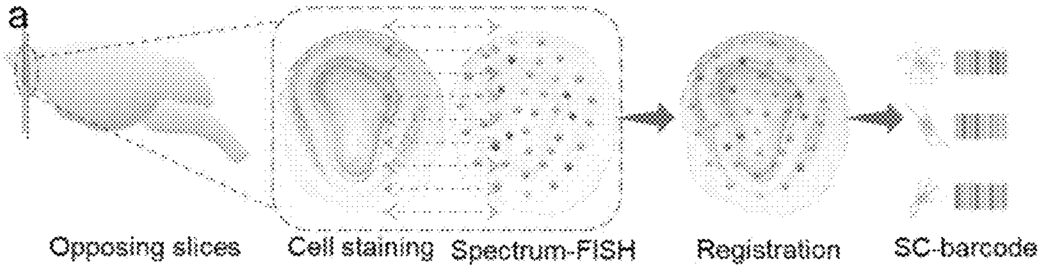
FIG. 7A schematically depicts main steps of correlating a spatial post-transcriptional profile with a corresponding registered cell-type specific labeled region of a target tissue, in olfactory bulb (OB), according to certain embodiments of the present invention.
Figure 7B:
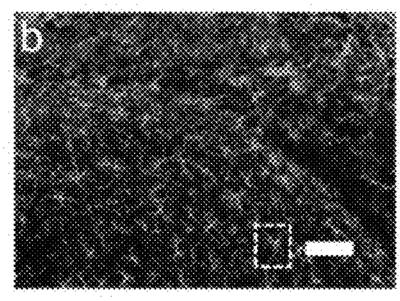
FIG. 7B shows a fluorescence image of the registered cell-type specific labeled tissue region prepared according to FIG. 7A; scale bar: 100 μm.
Figure 7C:
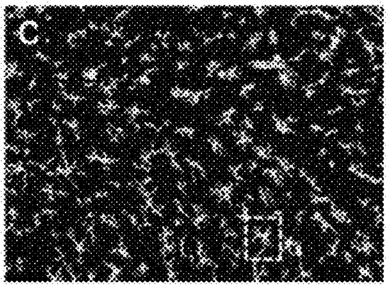
FIG. 7C shows a superimposed image of the fluorescence image in FIG. 7B with the spatial distribution of the nanoprobes across the registered cell-type specific labeled region.
Figure 7D:
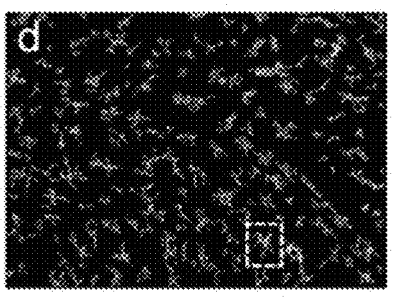
FIG. 7D shows the superimposed image of FIG. 7C overlaid with different spectrum codes from the corresponding nanoprobe-associated nanobeads.
Figure 7E:
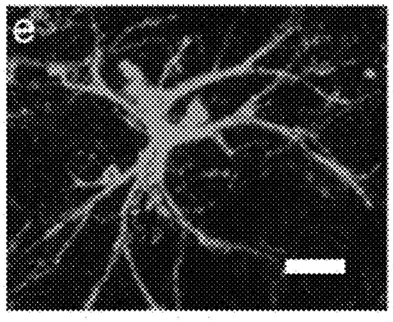
FIG. 7E shows an enlarged view of the image in FIG. 7B from the region defined by a dashed line box in FIG. 7D; scale bar: 10 μm.
Figure 7F:
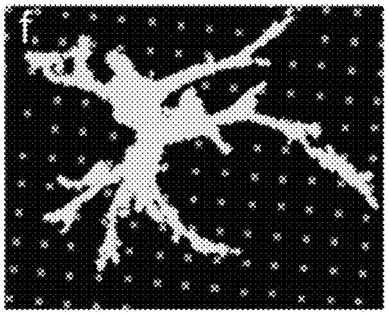
FIG. 7F shows an enlarged view of the superimposed image of FIG. 7C from the region defined by the dashed line box in FIG. 7D.
Figure 7G:
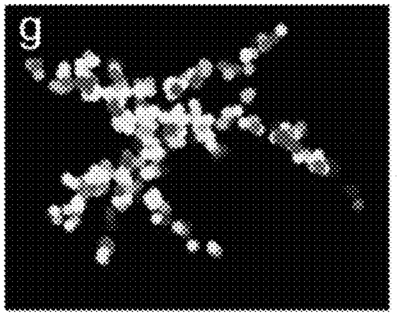
FIG. 7G shows an enlarged view of the superimposed image of FIG. 7D from the region defined by the dashed line box.
Figure 7H:
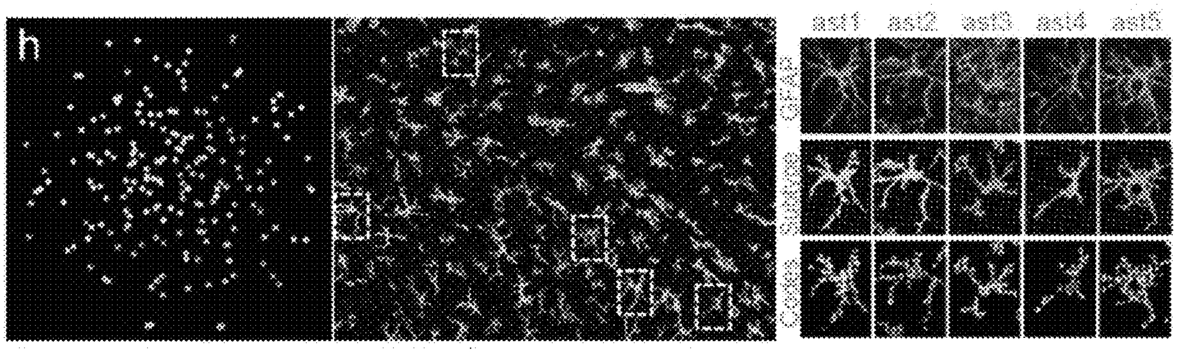
FIG. 7H shows cellular subtypes in astrocyte ($GFAP^+$) cells using unsupervised clustering of certain miRNA vectors: the left column shows a t-distributed stochastic neighbor embedding (t-SNE) distribution of the identified subtypes; the middle column shows the spatial distribution of different astrocyte subtypes in association with the nanoprobes; the right column shows the representative cellular morphology and the miRNA-specific spectrum code distributions for each astrocyte subtype (ast1, ast2, ast3, ast4 and ast5).
Figure 7I:
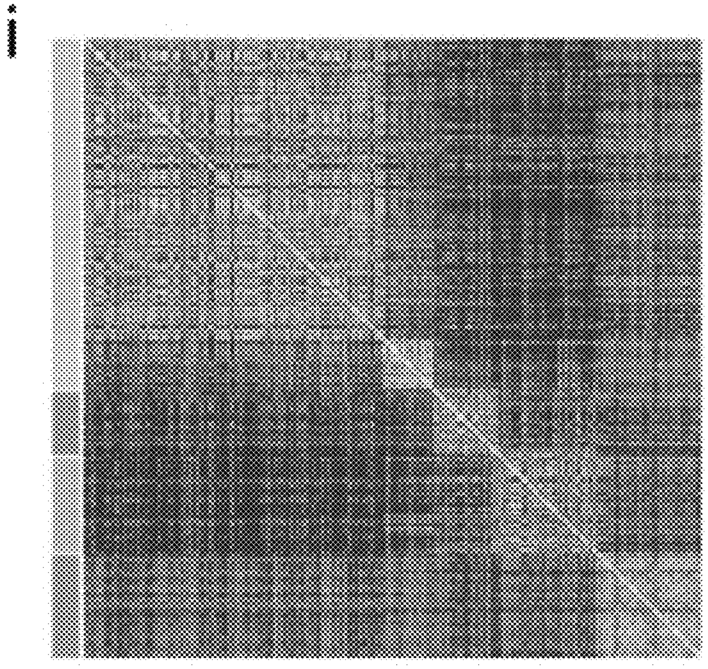
FIG. 7I shows a consensus matrix for a clustering analysis using pooled single-cell miRNA data.
Figure 7J:
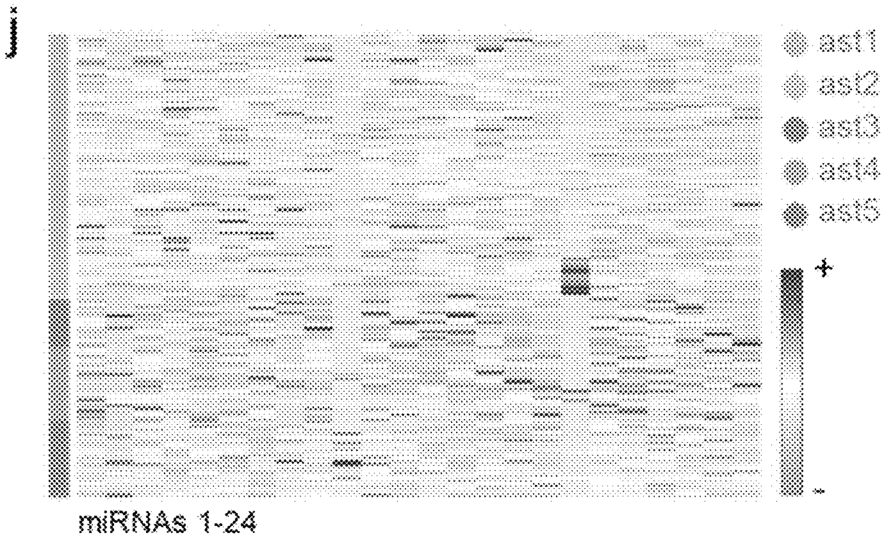
FIG. 7J shows an expression heatmap for expression of 24 miRNAs in the $GFAP^+$ cells and in each of the identified astrocyte subtypes.
Figure 8:
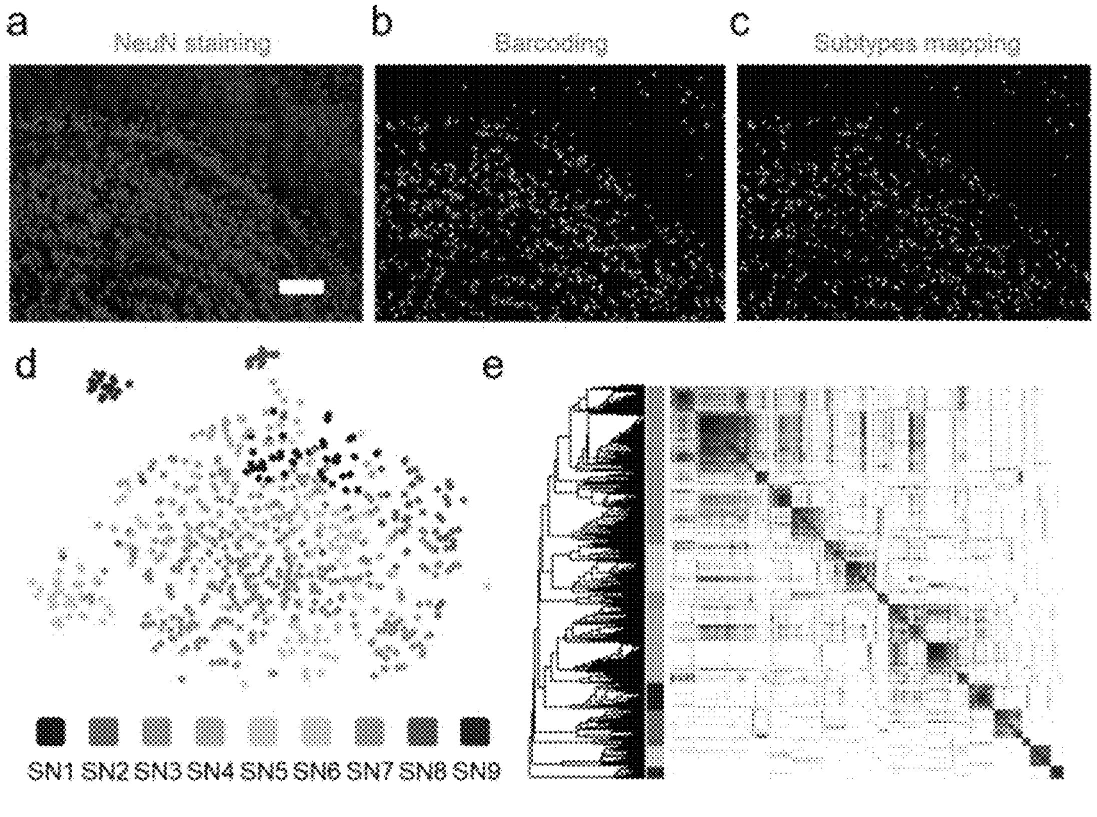
FIG. 8 shows the heterogeneity of extracted miRNAs for analyzing cellular subtypes in $NeuN^+$ cells of an OB tissue section: (a) immunofluorescence staining for NeuN (red fluorescence) to identify neuronal cells; scale bar: 100 μm; (b) superimposed image of the fluorescence image in (a) with the nanoprobe-associated nanobeads associated with miRNA-specific spectrum codes; (c) a t-SNE distribution of cellular subtypes in $NeuN^+$ cells using unsupervised clustering of certain miRNA vectors; (d) the clustering of $NeuN^+$ cells as shown in the t-SNE distribution of (c); (e) clustering heatmap showing the single cell analysis of miRNAs expressions in $NeuN^+$ cells.
Figure 16:
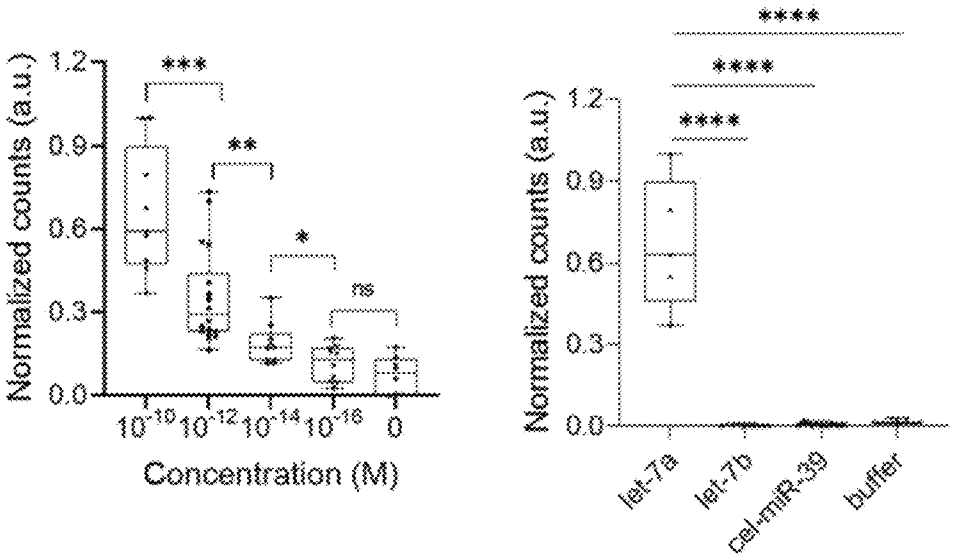
FIG. 16 shows a characterization of the detection sensitivity and specificity at different titers of samples: Unpaired t test, N>8, (left), N>5 (right); ** $p<0.0001$; * $p<0.001$; ** $p<0.01$; * $p<0.05$).

To correlate the resulted post-transcriptional miRNA profiles with the spatial distribution of individual cells, an acute OB tissue is sectioned into two opposing slices: one is immunostained with one or more cell-type specific markers (e.g., GFAP for astrocytes and NeuN for neurons) and the other is examined by the spectrum barcoding method of miRNA species. The results from the two opposing slices are then registered to give a full picture of the heterogeneous post-transcriptional miRNA regulation in the coordinates of all identified cells (FIG. 7*a*). The expression of 24 targeted miRNAs (Table 1) is analyzed. To accommodate such a throughput, three rounds of microscopic visualization are performed (as in FIG. 5A). In each round, a double stranded non-mammalian miRNA (cel-miR-39) is introduced to serve as an internal reference for data normalization, thus eliminating interference from systematic variations. For individual nanoprobes, the expression of extracted miRNAs is quantified by counting the beads of specific spectrum codes (FIG. 6C). The analytical sensitivity and specificity is sufficient to detect miRNAs down to $10^{-16}$ M and to differentiate targets with single nucleotide mismatch (FIG. 16). For a particular type of cells, such as the GFAP+ astrocytes, the nanoprobes that are in contact with each cell are respectively identified (FIG. 7*b-d*). For an individual cell, the subcellular distribution of particular miRNAs can be directly visualized by the distribution the nanobeads of corresponding spectrum code (FIG. 7*e-g*). From all nanoprobes under the umbrella of a specific cell, the number of miRNA-specific nanobeads is summed up and used as a quantification of the cell's overall expression. When the single-cell miRNA data is pooled together for an informatic analysis, different astrocyte groups (ast1-ast5) are revealed by unsupervised consensus clustering (FIG. 7*h-j*). While the biological basis for the identified astrocytes subpopulations is not clear, the results in the present disclosure suggest that the spatially distributed heterogeneity of post-transcriptional regulation appears in a particular cell type. Similar observation of neuronal sub-populations could also be derived by miRNA heterogeneity analysis in NeuN+ cells (certain subtypes of neuron cells) (FIG. 8).

TABLE 1

List of 24 examined miRNAs and their reporter sequences design:

| Name ID | Probe 5'-3' | Reporter biotin-5'-3' |
|---|---|---|
| mmu-miR-124-3p | GGCAUUCACCGCGUGCCUUACGCCA CGUGUUC (SEQ ID NO: 1) | TTTTTTGAACACGTGGCG (SEQ ID NO: 2) |
| mmu-miR-128-3p | AAAGAGACCGGUUCACUGUGAGUUA ACUGUUGA (SEQ ID NO: 3) | TTTTTTTCAACAGTTAAC (SEQ ID NO: 4) |
| mmu-miR-29b-3p | CACUGAUUUCAAAUGGUGCUAUUGG UGGCACAU (SEQ ID NO: 5) | TTTTTTATGTGCCACCAA (SEQ ID NO: 6) |
| mmu-miR-9-5p | AUACAGCUAGAUAACCAAAGAAAGU AAUACCAU (SEQ ID NO: 7) | TTTTTTATGGTATTACTT (SEQ ID NO: 8) |
| mmu-miR-29a-3p | AACCGAUUUCAGAUGGUGCUAGGUC CCUCAAAU (SEQ ID NO: 9) | TTTTTTATTTGAGGGACC (SEQ ID NO: 10) |
| mmu-miR-22-3p | CAGUUCUUCAACUGGCAGCUUCAUG CUAGCGUG (SEQ ID NO: 11) | TTTTTTCACGCTAGCATG (SEQ ID NO: 12) |
| mmu-let-7c-5p | ACCAUACAACCUACUACCUCAGCUA UCCAUAUG (SEQ ID NO: 13) | TTTTTTCATATGGATAGC (SEQ ID NO: 14) |
| mmu-miR-26a-5p | GCCUAUCCUGGAUUACUUGAAGUCC ACAGGACA (SEQ ID NO: 15) | TTTTTTTGTCCTGTGGAC (SEQ ID NO: 16) |
| mmu-let-7f-5p | ACUAUACAAUCUACUACCUCAGGAU UUACCCUU (SEQ ID NO: 17) | TTTTTTAAGGGTAAATCC (SEQ ID NO: 18) |
| mmu-let-7a-5p | ACUAUACAACCUACUACCUCAUAUG CGCCGGUU (SEQ ID NO: 19) | TTTTTTAACCGGCGCATA (SEQ ID NO: 20) |
| mmu-let-7g-5p | ACUGUACAAACUACUACCUCAUUCA GCCACGCU (SEQ ID NO: 21) | TTTTTTAGCGTGGCTGAA (SEQ ID NO: 22) |
| mmu-let-7b-5p | ACCACACAACCUACUACCUCAUAUG CCCAGCAU (SEQ ID NO: 23) | TTTTTTATGCTGGGCATA (SEQ ID NO: 24) |
| mmu-miR-29c-3p | AACCGAUUUCAAAUGGUGCUACGUU ACAACCAG (SEQ ID NO: 25) | TTTTTTCTGGTTGTAACG (SEQ ID NO: 26) |
| mmu-miR-181a-5p | UCACCGACAGCGUUGAAUGUUACCG AUACUAGA (SEQ ID NO: 27) | TTTTTTTCTAGTATCGGT (SEQ ID NO: 28) |
| mmu-miR-376a-3p | ACGUGGAUUUUCCUCUACGAUUGUA UAAAGUCC (SEQ ID NO: 29) | TTTTTTGGACTTTATACA (SEQ ID NO: 30) |
| mmu-miR-99a-5p | ACAAGAUCGGAUCUACGGGUUGCCA UGCAGACG (SEQ ID NO: 31) | TTTTTTCGTCTGCATGGC (SEQ ID NO: 32) |
| mmu-let-7d-5p | ACUAUGCAACCUACUACCUCUGAUU ACCGAGCA (SEQ ID NO: 33) | TTTTTTTGCTCGGTAATC (SEQ ID NO: 34) |
| mmu-miR-137-3p | ACGCGUAUUCUUAAGCAAUAAUUCU AUCAGGUC (SEQ ID NO: 35) | TTTTTTGACCTGATAGAA (SEQ ID NO: 36) |
| mmu-let-7e-5p | ACUAUACAACCUCCUACCUCAGGCG ACCACUAG (SEQ ID NO: 37) | TTTTTTCTAGTGGTCGCC (SEQ ID NO: 38) |
| mmu-miR-125b-5p | CACAAGUUAGGGUCUCAGGGAUGAG CUACUGGA (SEQ ID NO: 39) | TTTTTTTCCAGTAGCTCA (SEQ ID NO: 40) |

TABLE 1-continued

| List of 24 examined miRNAs and their reporter sequences design: | | |
|---|---|---|
| Name ID | Probe 5'-3' | Reporter biotin-5'-3' |
| mmu-miR-369-3p | AAAGAUCAACCAUGUAUUAUUUGCCG AGGGGUAA (SEQ ID NO: 41) | TTTTTTTTACCCCTCGGC (SEQ ID NO: 42) |
| mmu-miR-30a-5p | UUCCAGUCGAGGAUGUUUACACCAC GAUGCCGC (SEQ ID NO: 43) | TTTTTTGCGGCATCGTGG (SEQ ID NO: 44) |
| mmu-miR-127-3p | GCCAAGCUCAGACGGAUCCGAUAAG AACCUCUC (SEQ ID NO: 45) | TTTTTTGAGAGGTTCTTA (SEQ ID NO: 46) |
| mmu-miR-138-5p | GCCUGAUUCACAACACCAGCUGGUC GACGCAAG (SEQ ID NO: 47) | TTTTTTCTTGCGTCGACC (SEQ ID NO: 48) |

Figure 9:
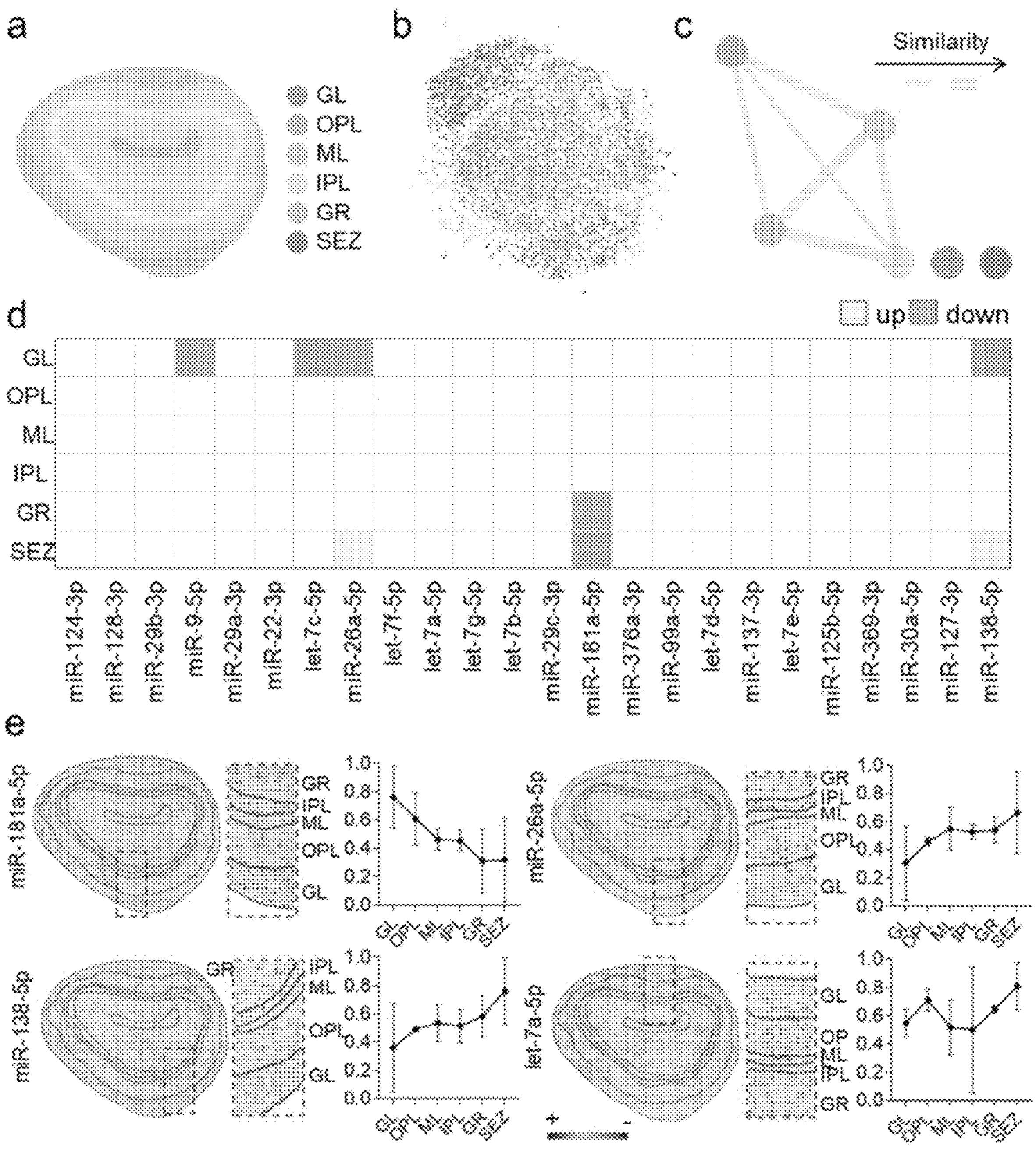
FIG. 9 shows spatial distribution of miRNA expression in different olfactory bulb (OB) regions: (a) labeling of six anatomical regions in a coronal OB slice; (b) coherence analysis of the miRNA vectors from different OB regions by using uniform manifold approximation and projection (UMAP); (c) a similarity network of the six OB regions derived by using the associated miRNA vectors, where shorter distance and thicker connection represent higher similarity in miRNA expression; (d) identification of the dominant miRNA signature (out of the 24 targets) for each OB region, where a comparison is made between one region versus all others, a signature was defined as a fold change greater than 1.1 and a $p<0.05$ by unpaired t-test. (e) a heatmap showing the representative spatial expression of a particular miRNA across a whole OB slice. The analysis was performed with a 4×4 binning of the nanoprobes, the error bars indicate mean±SD, data from more than 300000 nanoprobes were collected from three biological replicates.
Figure 17:
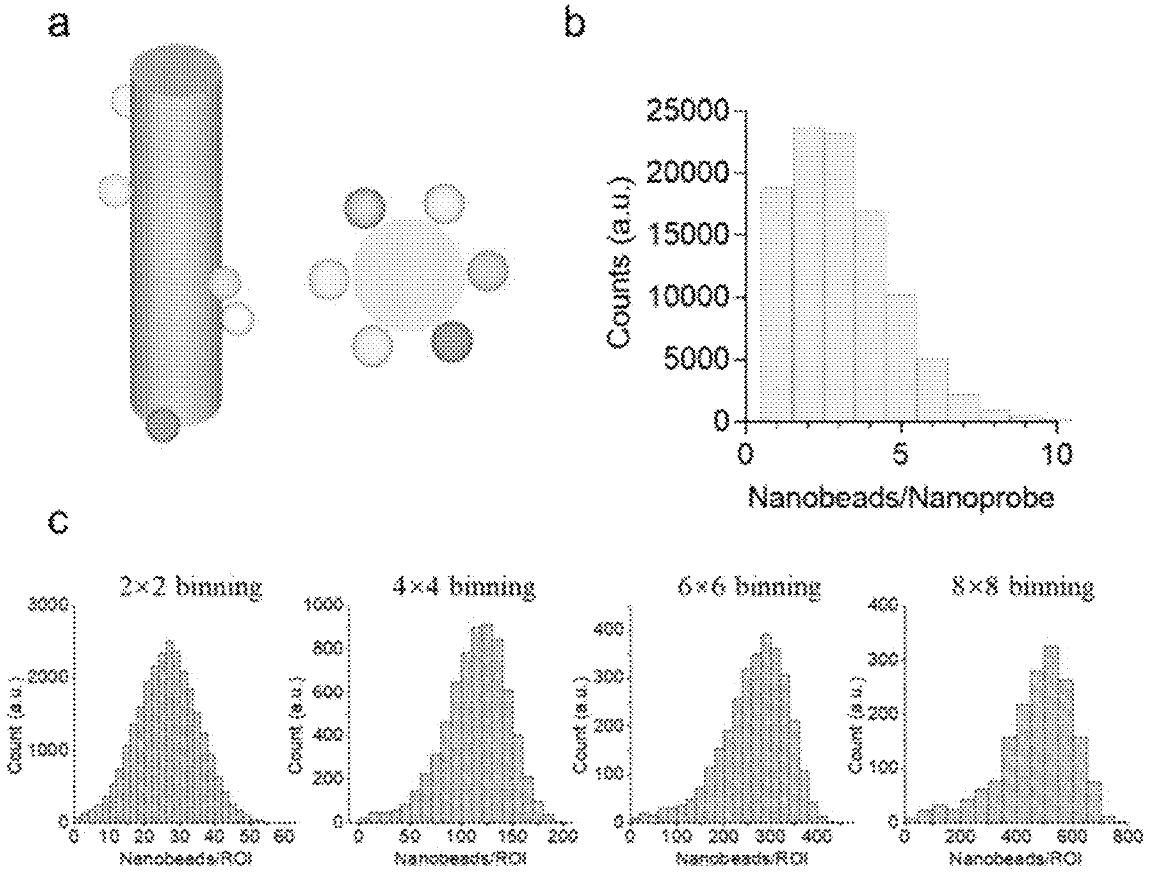
FIG. 17 shows analytical details of the spectrum codes acquired from the nanoprobes according to certain embodiments: (a) theoretical evaluation of the binding condition of nanobeads (300 nm in diameter) on individual nanoprobes (800 nm in diameter); (b) a histogram of the nanobead counts on individual nanoprobes; (c) effects of different binning on the quantification of nanobeads in the ROIs.

To fully unleash the power of the present invention for tissue-wide post-transcriptional profiling, the spatial expression of the 24 targeted miRNAs as shown in Table 1 across a whole coronal OB slice is analyzed. An OB slice is first labelled by six anatomical regions based on the Allen Brain Atlas (FIG. 9*a*), to which the spatial correlation of the nanoprobe-derived miRNA vectors is explored. For an OB slice as large as ~3 mm$^2$, signal from ~110000 nanoprobes is examined. In a computational analysis, the nanoprobes are processed with 4×4 binning (FIG. 17*c*), which effectively divide an OB slice into ~6800 regions of interest (ROIs, ~24×24 μm$^2$/each). From each ROI, a 24-dimensional miRNA vector is derived by the expression of the targeted 24 miRNAs. The miRNA vectors from different OB regions are first examined by uniform manifold approximation and projection (UMAP), which clearly show relatively more coherence for vectors in close spatial proximity (FIG. 9*b*). The computational analysis also shows a statistical similarity in miRNA expression among different OB regions, such as outer plexiform layer (OPL) vs. mitral layer (ML), granule layer (GR) vs. inner plexiform layer (IPL) or outer plexiform layer (OPL). The miRNA expression in the glomerular layer (GL) or subependymal zone (SEZ) show more distinctive patterns (FIG. 9*c*). The observed miRNA coherence could be reasonably explained by the spatial distance of neighboring OB regions. It also echoes some previous reports that documented similar cellular composition in OPL, ML, IPL and GR.

To identify the dominant miRNA signature out of the 24 targets in Table 1, for each OB region, the expression of a particular miRNA (average from all associated nanoprobes) is statistically compared across the six OB regions (FIG. 9*d*). The statistic shows that miR-181a-5p is down-regulated in GR and SEZ, and there is a general decreasing expression level of miR-181a-5p across the outer to inner region of OB. On the contrary, a significant up-regulation of miR-138-5p is observed at the most inner part of OB in the SEZ layer, and an increasing expression pattern is observed across GL to SEZ regions; similar trend is also found with miR-26a-5p (FIG. 9*e*). Interestingly, let-7a-5p shows a relatively even distribution across different OB regions, suggesting different roles of particular miRNAs for a heterogeneous spatial regulation in the OB.

Figure 10:
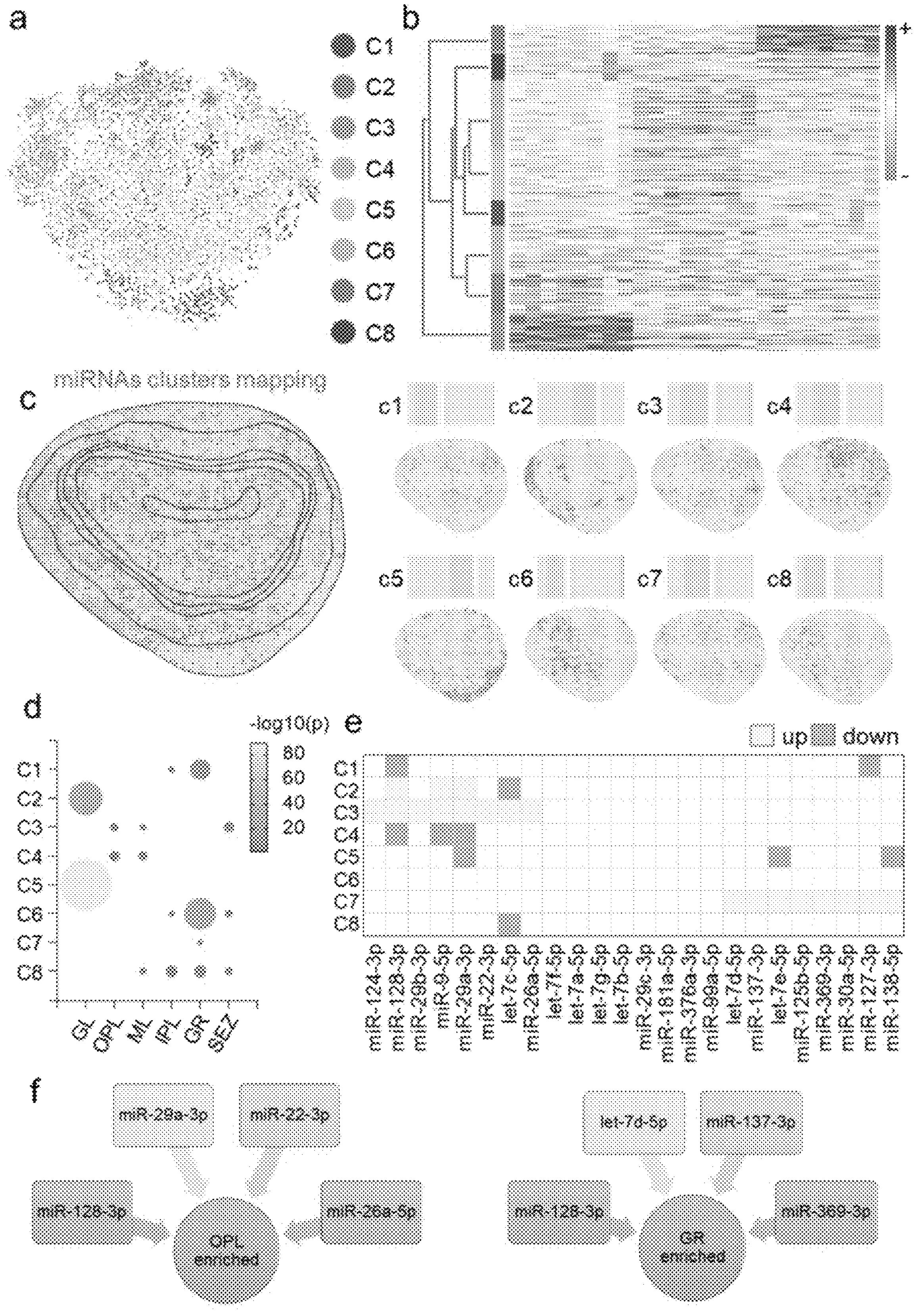
FIG. 10 shows a clustering analysis of miRNA spatial heterogeneity in an OB tissue section: (a) a t-SNE visualization of the eight miRNA clusters derived by unsupervised BayesSpace clustering; (b) a heatmap showing normalized miRNAs expression of the 8 clusters with the dendrogram tree indicating their hierarchical similarity; (c) mapping of the spatial distribution of 8 miRNA clusters in an OB structure atlas, where the split subpanels (right) show the mapping of individual miRNA clusters and the corresponding enrichment in different OB sub-regions; (d) Visualization of the enrichment analysis of the 8 clusters in six OB sub-regions by using hypergeometric test. The dot size and color indicate regional enrichment, which is derived from the P value of the hypergeometric test; (e) Identification of the miRNA signature (out of the 24 targets) for different miRNA clusters. The comparison was made between one cluster versus all others, a signature was defined as a fold change greater than 1.5 and a $p<0.05$ by unpaired t-test; (f) Visualization of the potential correlation between the miRNA cluster signature and spatial enrichment in specific OB sub-regions (OPL and GR); data from more than ~300000 nanoprobes were collected from three biological replicates.
Figure 11:
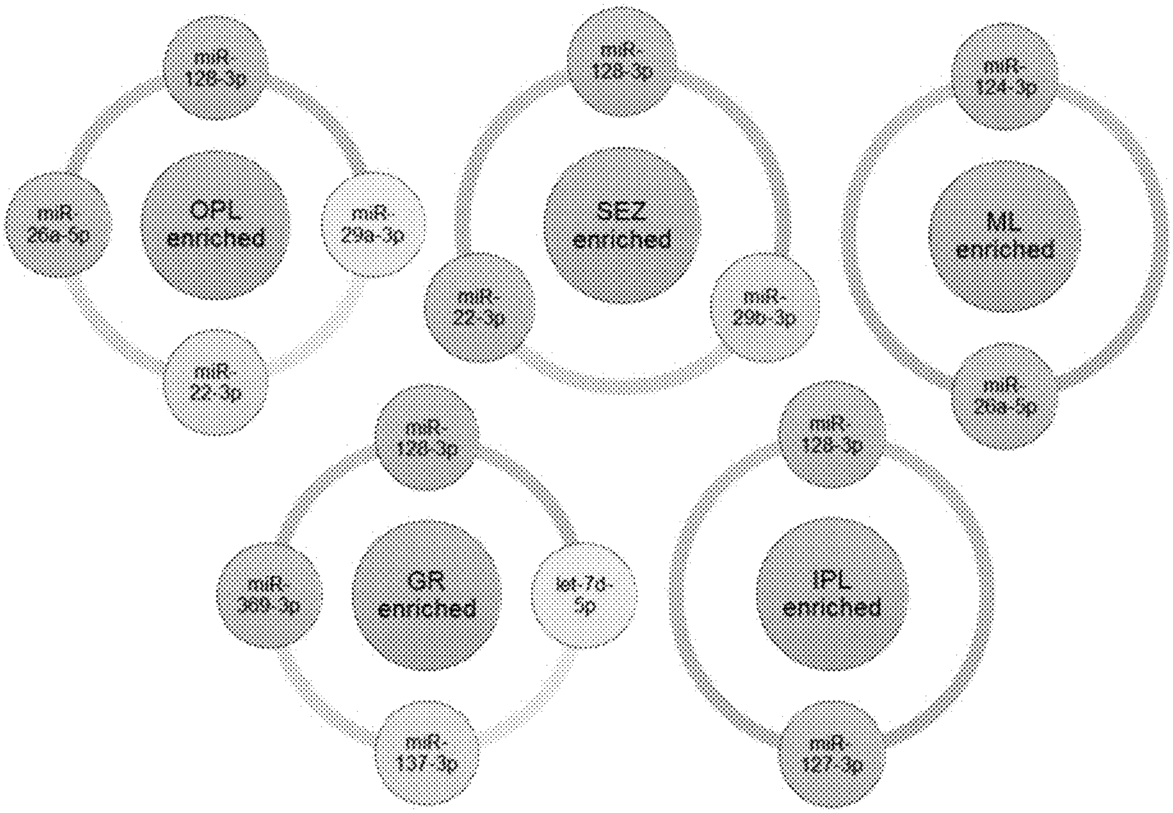
FIG. 11 schematically depicts a potential correlation between different miRNA signatures for a cluster and its associated spatial enrichment in different OB sub-regions.

To further explore an intrinsic spatial miRNA patterning, unsupervised BayesSpace clustering analysis is performed without prior OB structural labelling. As shown in FIG. 10*a-b*, all the miRNA vectors acquired from the ~6800 ROIs are identified and grouped into 8 clusters solely based on the miRNA expression coherence (C1-C8). The spatial distribution of these clusters is identified to show significant enrichment in particular OB anatomic regions (FIG. 10*c*), which can be statistically confirmed by a hypergeometric test (FIG. 10*d*). For example, miRNA cluster 2 (miR-C2) and miR-C5 are significantly enriched in GL; miR-C3 and miR-C4 are slightly enriched in OPL and ML; miR-C1 and miR-C6 are obviously enriched in GR. For each identified miRNA clusters, the most phenotypic signature miRNAs were then determined (FIG. 10*e*). These analytical results suggest that some miRNAs are particularly important for the spatially heterogeneous post-transcriptional regulation in OB than the others, especially in the region of OPL and GR (FIGS. 10*f* and 11).

Figure 18:
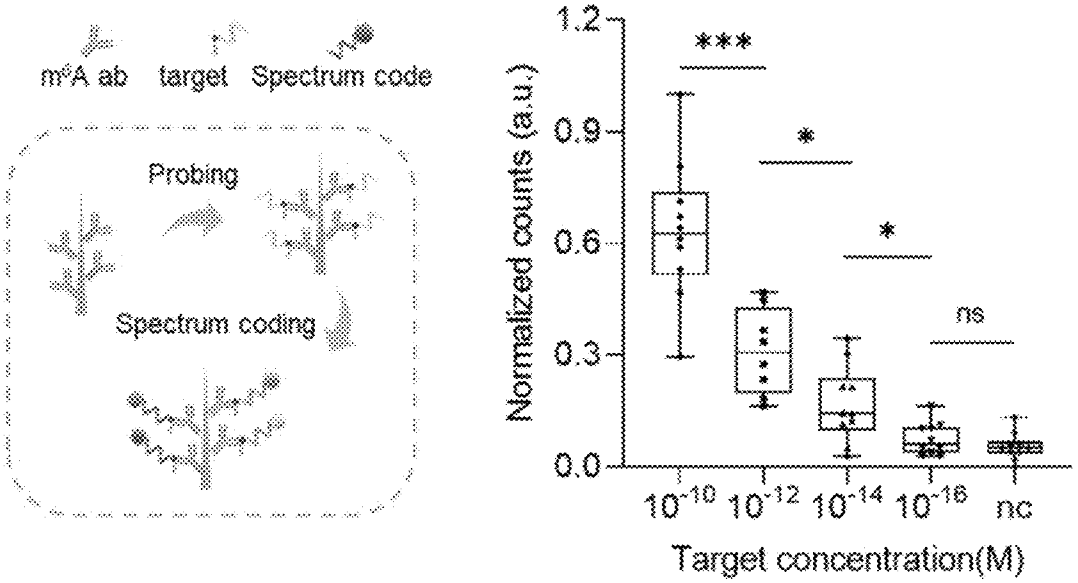
FIG. 18 shows nanoprobe functionalization strategy for molecular fishing of $m^6A$-mRNAs using specific antibodies as the "bait" protein (left panel) and characterization of the detection sensitivity for $m^6A$-mRNAs by using the spectrum barcoding system (right panel); Unpaired t-test, N>8, *** $p<0.001$; * $p<0.05$.

In addition to miRNAs, other post-transcriptional targets such as RNA methylations are also analyzed by the present invention so that the spatial cooperative involvement of different post-transcriptional mechanisms can be verified. To apply the present system in determining spatial profiling of RNA methylation, 9 mRNAs with m$^6$A methylation are targeted in an acute coronal OB slice (Table 2). The "bait" protein (p19 for miRNAs) associated with the nanoprobes should be replaced by m$^6$A-specific antibodies, and the nanoprobe associated operations described herein remains unchanged. The m$^6$A-specific antibodies can extract all m$^6$A-methylated RNAs, which are later decoded by an on-chip (in-situ) analysis and quantification (FIG. 18).

TABLE 2

| List of 9 examined m$^6$A-mRNAs and their reporter sequences design: | | |
|---|---|---|
| Gene | Reference sequence 5'-3' | Reporter biotin-5'-3' |
| Myo16-m$^6$A | CACCTCCTTTGTTTTTAGA GACTCGAAAAGCCATCATC TTG (SEQ ID NO: 49) | *AAACTACGATGG*CAA GATGATGGCTTTTCG (SEQ ID NO: 50) |
| Gng4-m$^6$A | AAGCCTTGAGATTTTCCAT GACAAGGCTGTTGGCCCCA TCT (SEQ ID NO: 51) | *AAACTACGATGG*AGA TGGGGCCAACAGCCT (SEQ ID NO: 52) |
| Fam184a-m$^6$A | GCTGGCACAGCTCTGTGTG GACTGTTCCAAGAGCATGA CTG (SEQ ID NO: 53) | *AAACTACGATGG*CAG TCATGCTCTTGGAAC (SEQ ID NO: 54) |
| Nmb-m$^6$A | GTGTCCATCCAGGGAAGCT GACAATGGAACCCTAGCAG TGG (SEQ ID NO: 55) | *AAACTACGATGG*CCA CTGCTAGGGTTCCAT ((SEQ ID NO: 56) |

TABLE 2-continued

List of 9 examined $m^6A$-mRNAs and their reporter sequences design:

| Gene | Reference sequence 5'-3' | Reporter biotin-5'-3' |
|---|---|---|
| Gcnt1-$m^6A$ | GAGGCATAAAGCCCTGGAG AACTTAGAACACTAAGCGC TGC (SEQ ID NO: 57) | *AAACTACGATGG*GCA GCGCTTAGTGTTCTA (SEQ ID NO: 58) |
| Prox1-$m^6A$ | CGGCTCCTTCTCGGGGAAG GACAGAGCCTCTCCTGAGT CCT (SEQ ID NO: 59) | *AAACTACGATGG*AGG ACTCAGGAGAGGCTC (SEQ ID NO: 60) |
| Gpr161-$m^6A$ | TGCCACCCTCTGATCTACG GACTCTGGAACAAGACTGT GCG (SEQ ID NO: 61) | *AAACTACGATGG*CGC ACAGTCTTGTTCCAG (SEQ ID NO: 62) |
| Epha7-$m^6A$ | TGGCCAGGAACACAGCAGA GACAATAAACAAAGTACTA CCT (SEQ ID NO: 63) | *AAACTACGATGG*AGG TAGTACTTTGTTTAT (SEQ ID NO: 64) |
| Zbtb20-$m^6A$ | AACGACAACAAAAGAAATA AACAAGCAAACAAACAGAC AAA (SEQ ID NO: 65) | *AAACTACGATGG*TTT GTCTGTTTGTTTGCT (SEQ ID NO: 66) |

Figure 12:
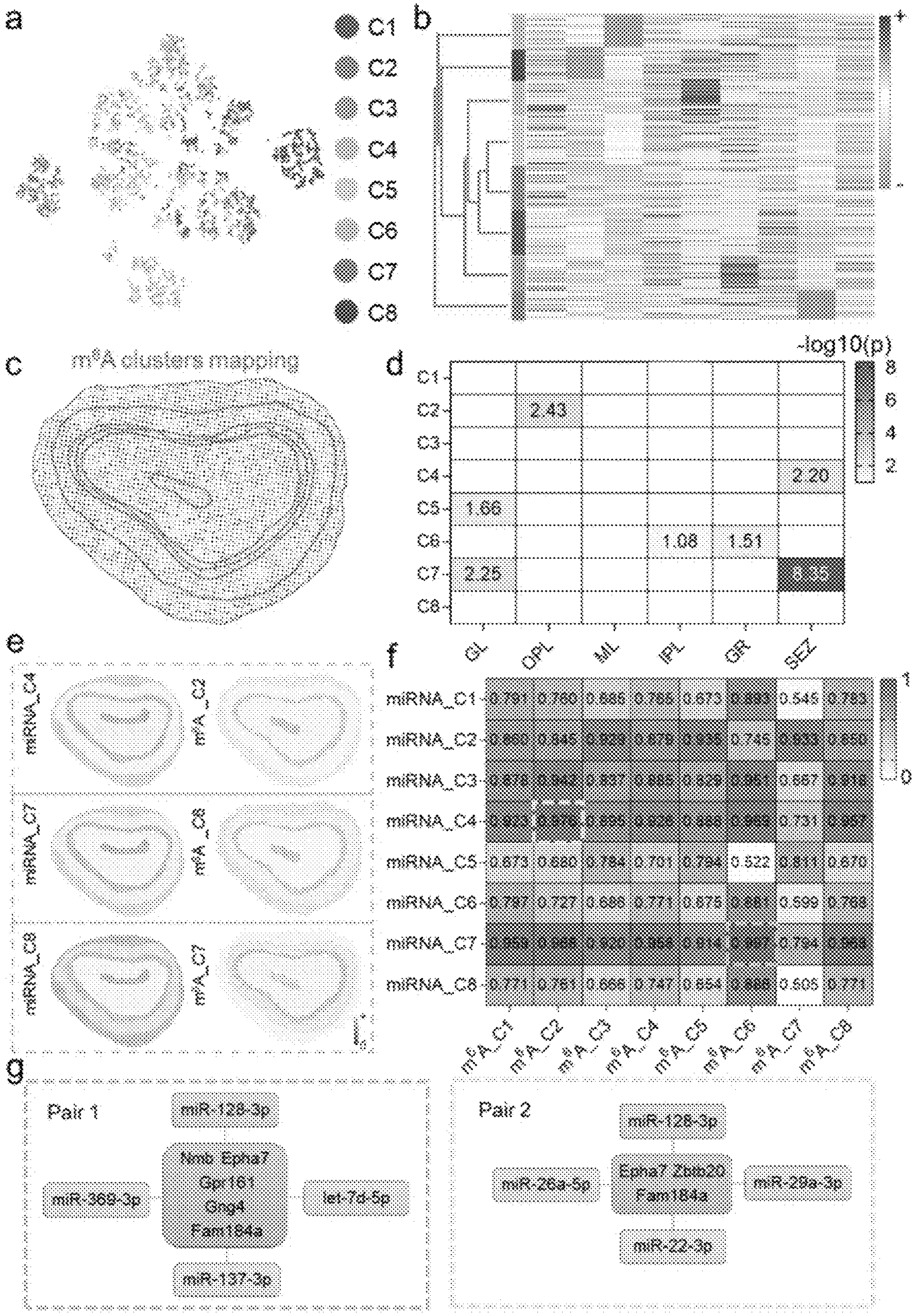
FIG. 12 shows a tissue-wide spatial heterogeneity of RNA methylation in an OB tissue section: (a) a t-SNE visualization of the eight $m^6A$-mRNA clusters derived by unsupervised BayesSpace clustering; (b) a heatmap showing normalized expression the 9 $m^6A$-mRNAs for the 8 identified $m^6A$-mRNA clusters with the dendrogram tree indicating their hierarchical similarity; (c) mapping of the spatial distribution of 8 $m^6A$-mRNA clusters in an OB structure atlas; (d) analysis of the spatial enrichment of each $m^6A$-mRNA clusters in six OB sub-regions by using the hypergeometric test; (e) Visualization of representative spatial distribution vectors (SDV) for coupled miRNA and $m^6A$-mRNA clusters; (f) Analysis of spatial correlations between paired miRNA- and $m^6A$-mRNA clusters with Pearson correlation coefficient; (g) identification of potential cooperative involvement of paired miRNAs and methylated mRNAs in different OB sub-regions.
Figure 13:
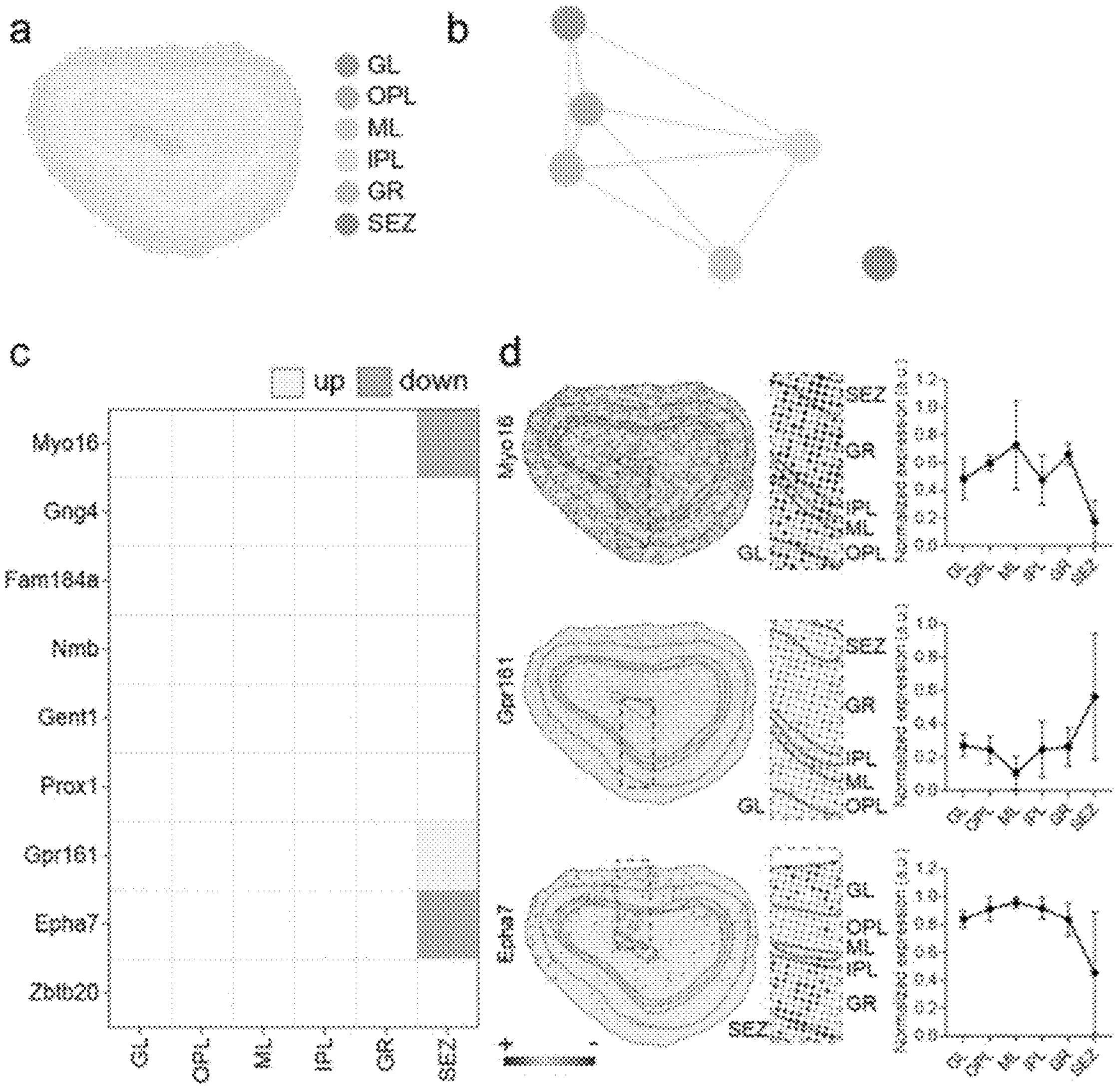
FIG. 13 shows a regional organization of $m^6A$-mRNAs in an OB tissue section: (a) labeling of six anatomical regions in a coronal OB slice; (b) a similarity network of the six OB regions derived by using the associated $m^6A$-mRNA data, where shorter distance and thicker connection represent higher similarity in $m^6A$-mRNA expression; (c) identification of the dominant $m^6A$-mRNAs (out of the 9 targets) for each OB sub-region, where a comparison is made between one region versus all others, a significant target was defined as a fold change greater than 1.1 and a $p<0.05$ by unpaired t-test; (d) representative spatial expression of a particular $m^6A$-mRNA across a whole OB section, where the analysis is performed with a 4×4 binning of the nanoprobes, the error bars indicate mean±SD, data from more than ~200,000 nanoprobes were collected from three biological replicates.
Figure 14:
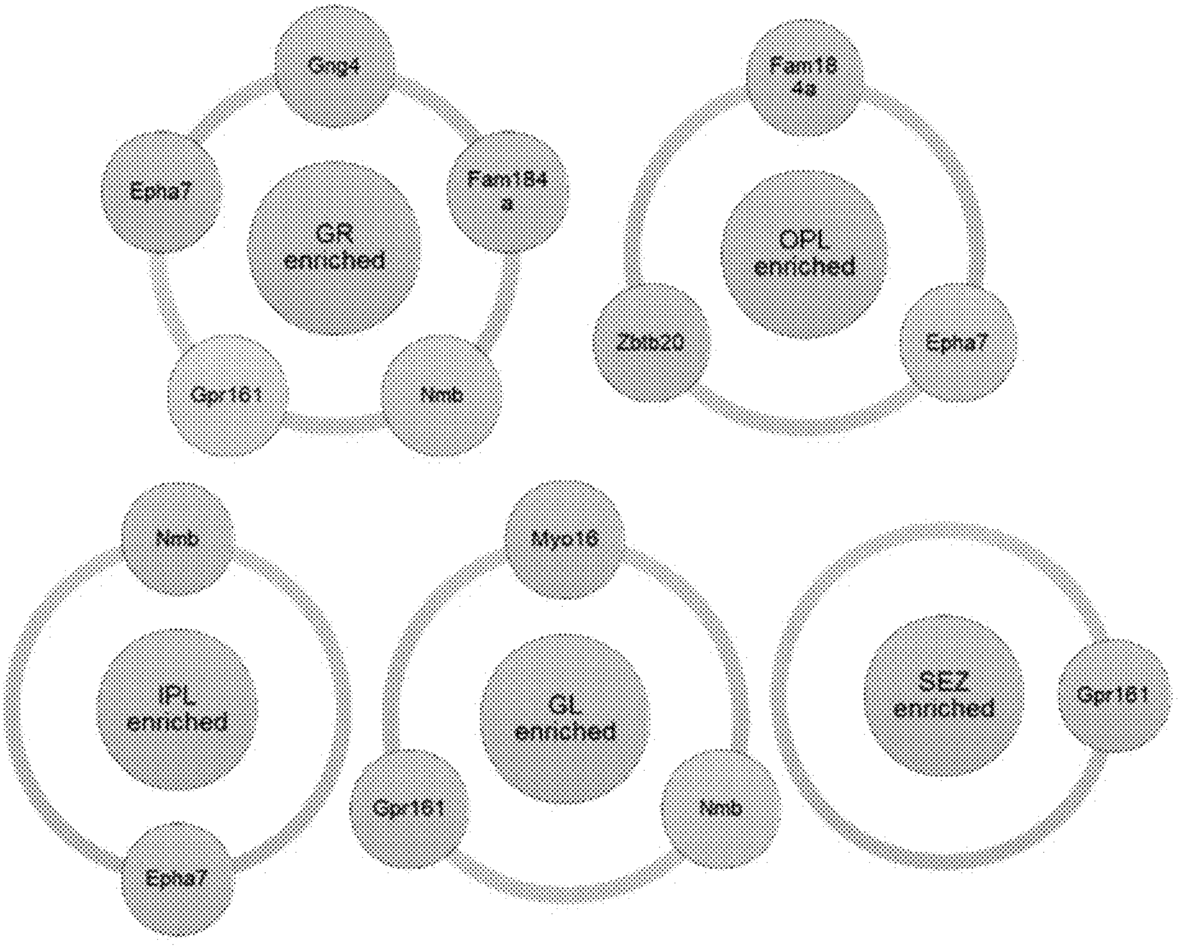
FIG. 14 schematically depicts a potential correlation between the $m^6A$-mRNA signature for a cluster and its associated spatial enrichment in different OB sub-regions.

*Bolded base represents methylation site; underlined bases represent sequence for capture; italic bases represent 5'-repeats The expression of the 9 $m^6A$-mRNAs in different OB sub-regions is firstly examined, showing a unique pattern in SEZ in comparison to other OB regions (OPL, ML, IPL and GR) with significant upregulation of $m^6A$-Gpr161 and down-regulation of $m^6A$-Epha7 in SEZ. Such observation is further confirmed by a spatial mapping of these $m^6A$-mRNAs (FIG. 13). Using the unsupervised clustering analysis described herein, the 9-dimensional $m^6A$-mRNA vectors (from all nanoprobes covered by an OB slice) are self-grouped into 8 clusters ($m^6A$-C1~$m^6A$-C8, as in FIG. 12*a-c*), of which $m^6A$-C4 and $m^6A$-C7 are particularly enriched in SEZ. Meanwhile, at a moderate level, $m^6A$-C2 is enriched in OPL; $m^6A$-C5 and $m^6A$-C7 are enriched in GL, and $m^6A$-C6 is enriched in GR (FIG. 12*d*). These results further show a substantial heterogeneity in mRNA methylation at different OB regions, suggesting a complex role of associated translational regulation of cellular function (FIG. 14).

Some studies found that $m^6A$ methylation of mRNAs can be regulated by miRNAs via a sequence pairing mechanism to modulate the binding between methyltransferase and mRNAs. The versatility of the spectrum barcoding system and related decoding method provide an extra dimension to demonstrate the cooperative involvement of the two post-transcriptional regulatory mechanisms across a whole tissue sample. A spatial distribution vector (SDV) for each of the miRNA clusters and $m^6A$-mRNA clusters is generated (FIG. 12*e*), which can be used to derive the spatial correlations between paired miRNA- and $m^6A$-mRNA clusters (FIG. 12*f*). As seen, miRNA-C7 and $m^6A$-C6 pair shows the highest spatial correlation, and both clusters are identified to enrich in GR (FIGS. 11*d* & 12*d*), indicating a high level of cooperation between the associated miRNAs and $m^6A$ methylation in the region. Another highly correlated pair is miRNA_C4 and $m^6A$_C2, which are enriched in OPL (FIGS. 11*d* & 12*d*). Considering the signature targets in different miRNA- or $m^6A$-clusters, it would be interesting to further explore the potential interactive roles of paired miRNAs and methylated mRNAs (FIG. 12*g*), especially in GR or OPL region of the OB.

EXAMPLES (A) Nanoprobe Functionalization

Figure 2A:
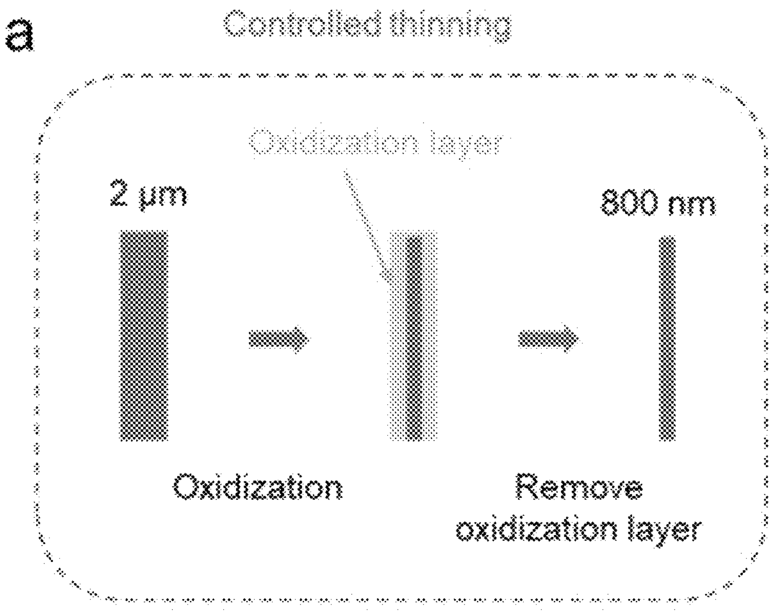
FIG. 2A schematically depicts fabrication process of nanoprobes from silicon material according to certain embodiments of the present invention.
Figure 2B:
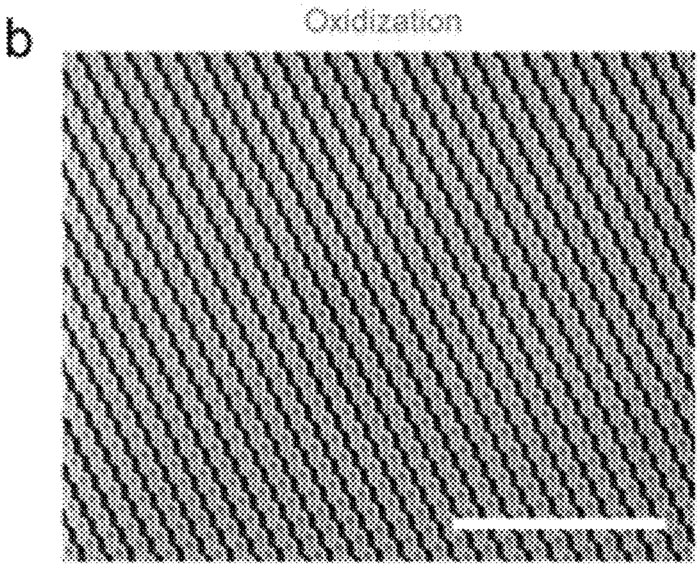
FIG. 2B shows an SEM image of the oxidized silicon nanoprobes prepared according to the fabrication process depicted in FIG. 2A; scale bar: 50 μm.
Figure 2C:
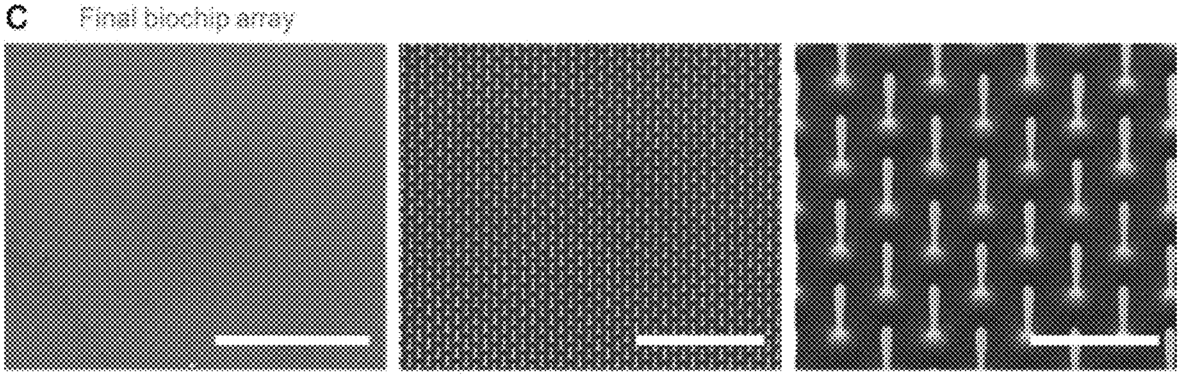
FIG. 2C shows SEM images of the final silicon nanoprobes prepared according to the fabrication process depicted in FIG. 2A at different magnifications; scale bars: 400 μm (left), 50 μm (middle), 10 μm (right).
Figure 2D:
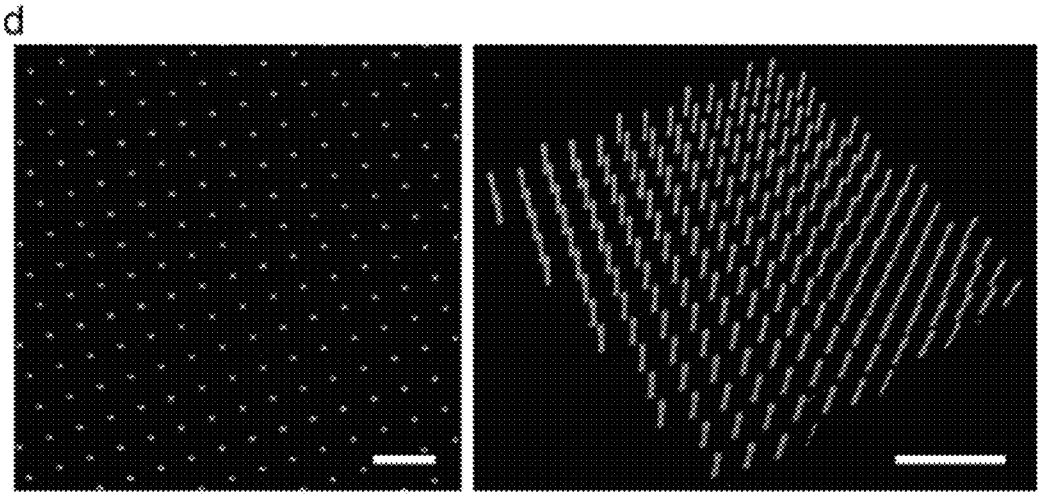
FIG. 2D shows green fluorescence images of the final nanoprobes prepared according to the fabrication process depicted in FIG. 2A at different perspectives and magnifications: scale bars: 10 μm (left, top view), 20 μm (right, perspective view).

As illustrated in FIG. 2A, a silicon-based nanoprobe array was fabricated from silicon wafers using a top-down approach. Array dots with 2 μm were printed using photolithographically on a silicon wafer. Then a micropillar array (diameter: 2 μm; height: 9 μm) was produced by deep reactive ion etching. Nanoneedles were produced by thinning down the pillars using thermal wet oxidization at 1100° C. (10 h) and buffered hydrogen fluoride (BHF) etching. The final nanoneedle array has diameter of ~800 nm, height of ~7 μm and interval space of ~5 μm As illustrated in FIG. 3, the silicon nanoprobe array were further cut into squares (5 mm×5 mm) and then processed with piranha solution (v/v=3:1, 98% $H_2SO_4$:27.5% $H_2O_2$) at 90° C. for 90 mins. The chips were subsequently washed with deionized water, methanol, methanol/dichloride methane (DCM) mixture (v/v=3:1) and DCM. (3-aminopropyl) triethoxysilane with a volume fraction of 3% in DCM was used to further functionalize the chips with amino functional groups for 3 hours. Afterward, the chips were washed by ethanol, isopropyl alcohol and deionized water subsequently.

The amino functionalized chips were activated using glutaraldehyde (15%, v/v) for 2 hours and then crosslinked with p19 siRNA binding protein (1 μg/ml in depc-PBS; New England Biolabs) or anti-N6-methyladenosine ($m^6A$) antibody (1 μg/ml in depc-PBS, Abcam) for 2 hours. BSA (1%, m/m in depc-PBS) and triton X100 (0.1%, v/v, in depc-PBS) mixture were used to block the unreacted groups of the chips for 5 hours. The chips were further reacted with PC biotin-PEG3-NHS ester (0.2 mg/ml, Sigma-Aldrich) for 1 hour and then then labeled with streptavidin conjugated with Alexa Fluor™ 568 (0.04 mg/ml in depc-PBS, ThermoFisher) for 1 hour, followed with treating with unlabeled biotin (0.1 mg/ml) for another 2 hours to block the unreacted streptavidin sites. All the reactions were performed in room temperature unless specifically mentioned.

(B) Spectrum Codes Fabrication

50 μL amino magnetic beads (J&K, 300-400 nm diameter, in PBS) were used for the spectrum codes preparation followed by reacting with 1 μL biotin-NHS (Sigma, 2 mg/mL) for 2 hours in room temperature. The beads were then washed three times using depc-PBS and 5 μL diverse type of streptavidin conjugated with specific fluorophores (i.e. Streptavidin, ALEXA FLUOR™ 488 conjugate, Streptavidin, ALEXA FLUOR™ 514 conjugate, Streptavidin, ALEXA FLUOR™ 555 conjugate, Streptavidin, ALEXA FLUOR™ 647 conjugate, ThermoFisher, 2 mg/mL) were mixed together with biotin functionalized beads for 2 hours at room temperature. Depc-PBS was used to wash the beads three times and 4 μL corresponding 5'-biotin DNA probe (BGI, 100 μM) was mixed with the beads for 2 hours, followed by treating with unlabeled biotin (0.1 mg/ml) for another 2 hours to block the unreacted streptavidin. After washing three times with depc-PBS, the beads were dispersed in 50 μL 1% BSA and 0.1% trition X100 solution and stored in 4° C. for further applications.

Optionally, the binding process can be achieved in several widely used methods, e.g., a) Electrostatic adhesion. In this condition, the particles surface will carry opposite charges with that of fluorophores. For example, if the fluorophores have negative surface charge in solution and the particles have positive charges, they will tend to bind with each other by the electrostatic adhesion. b) Absorption. If the particles are porous, then the fluorophores can be absorbed within the pores to achieve the binding status between particles and fluorophores. c) Other crosslinking mechanisms. Other than the above-mentioned biotin-streptavidin pair fluorophores and particle can both have amino group and can be cross-linked via glutaraldehyde or NHS-PEG-NHS or via NHS-NH2 reaction, for example, AF-488-NHS with amino-$Fe_3O_4$ particles.

(C) Spatial Probing of miRNAs Via Intracellular Biopsy

All the complementary miRNA probes with overhang were mixed with a concentration of $10^{-8}$ M in hybridization buffer (1%, m/m, BSA, 0.01%, v/v, tween 20, 5×SSC), followed by adding miR-cel 39 (10-10M) as internal reference and hybridize with the complementary probe for 15 min in 37° C. water bath.

For preparing the tissue sample, C57BL/6 mice (4-6 weeks) were sacrificed by cervical dislocation. The brains were harvested and maintained in ice-cold depc-PBS buffer, mounted on a vibratome with glue, and then were cut into coronal slices each of 500 μm thick.

Acute brain slice was rinsed with depc-PBS for several times and then transfer under the needle chip immersed with the prepared probes in a four well plate. The plate was centrifuged at 500 rpm (35.5 g of RCF, same below) for 5 mins to initiate a membrane puncture. The slices (or cells) with the nanoprobe patch were incubated 15 mins before miRNA target extraction in 37° C. The sample again underwent a centrifugation at 500 rpm for 10 mins to fish targeted miRNAs from brain slices (or cells) for further analysis.

After intracellular fishing, the needle chip with tissue on the top was transferred in depc-PBS with 0.1% tween 20 and exposed to 5 mW UV for 20 mins to imprint the tissue outline. A digital photograph was also captured to record the tissue and needle spatial relative location as an auxiliary registration method complementary to the UV imprint. Then the tissue was removed from the needle chip. Barcodes with different reporter probes were used to label the targets in the needle chip for 2 hours. Leica SP8 with 63×oil objective was used for imaging.

(D) Spatial Probing of $m^6A$ mRNAs Via Intracellular Biopsy

Acute brain slice was rinsed with depc-PBS for several times and then transfer under the needle chip immersed with the prepared probes in a four well plate. The plate was centrifuged at 500 rpm (35.5 g of RCF, same below) for 15 mins to fish targeted m6a mRNAs from brain slices (or cells) for further analysis.

After intracellular fishing, the needle chip with tissue on the top was transferred in depc-PBS with 0.1% tween 20 and exposed to 5 $mW/cm^2$ UV for 20 mins to imprint the tissue outline. A digital photograph was also captured to record the tissue and needle spatial relative location as an auxiliary registration method complementary to the UV imprint. Then the tissue was removed from the needle chip. Barcodes with different reporter probes were used to label the targets in the needle chip for 2 hours. Leica SP8 with 63×oil-immersion objective was used for imaging.

(E) Strip and Re-Hybridization

After finishing imaging of one round, DNase I (ThermoFisher) was used to digest the reporter probes and strip the barcodes in 37° C. for 30 mins. The needle chip sonicated in triton X100 (0.25%, v/v, in depc-DI) for 30 s and washed with depc-PBS for three times. Another round of barcode with reporter probes were used to label the targets of the needle chip. Besides DNase I, other enzymes such as NaOH or formamide may be used.

(F) Image Processing and Analysis

Confocal microscope (Leica) equipped with 63× oil-immersion objective was used for imaging. Registration of tissue and needle array were performed in Photoshop and Matlab image processing toolbox using the UV imprint outline, digital photo and the tissue immunofluorescence staining image. The labelled brain region of the staining image was performed in Photoshop based on Allen brain atlas. For the single cell analysis, watershed segmentation in Fiji was used to process the NeuN stained image. The segmentation of the GFAP stained image was performed by adaptive binarization in Matlab. For decoding the barcodes, a threshold was optimized for the fluorescence image binarization. ROIs were extracted to generate barcode feature vectors for the further decoding using ML model.

(G) Immunofluorescent Staining Based Single Cell Subtype Clustering and Mapping

The miRNAs or $m^6A$ mRNAs barcode pattern was registered with the binarized astrocyte or neuron mask. The connected domains were analyzed with 'bwlabel' and 'regionprops' in Matlab. The copy number of the miRNAs or $m^6A$ mRNAs were calculated and normalized by dividing the correspond cell area. The single cell expression matrix was extracted and cluster analysis for the single cell subtype cluster was performed in R using the ConsensusClusterPlus package, The optimized cluster number was selected based on the CDF delta area plot using the usual elbow method.

(H) Conjoint Analysis of miRNA-mRNA Spatial Correlation and Target Relationship

Similar unsupervised cluster analysis was performed for both miRNAs and $m^6A$ mRNAs using BayesSpace R package[2]. The enrichment of the clusters in related brain regions were calculated with hypergeometric test. Spatial distribution vector (SDV) of miRNAs or $m^6A$ mRNAs were calculated based on the distribution ratio of each cluster on the six brain regions. The correlation map of miRNAs and $m^6A$ mRNAs were then calculated with the generated SDV for each two-cluster pair. Cluster pair with high correlation was selected for further analysis.

(I) Selection and Design of $m^6A$ mRNA Probes

Target mRNAs were designated using the database from Allen Brain Atlas. Top differential fold change mRNAs in main olfactory bulb with high confidence m6A sites were selected for the further profiling. $m^6A$-Atlas was used to identify the high-confidence $m^6A$ sites of specific mRNAs. Database from PA-$m^6A$-seq, miCLIP, DART-seq, $m^6A$-CLIP-seq, $m^6A$-REF-seq, MAZTER-seq and $m^6A$-seq with improved protocol were applied for reference. A 41 bp reference sequence was acquired and based on which, the related reporter probes for specific $m^6A$ mRNAs were designed.

(J) Spectral Digitalization Barcoding and Encoding Strategy

Fluorophores with different excitation wavelengths or emission wavelengths were selected for barcoding. 300-400 nm beads were used as coding media, which can be easily imaged in common confocal microscope. Machine learning (ML) algorithms were used for decoding with each fluorophore channel as a feature vector input. A simple way was initially considered to judge the existence of fluorophore directly by setting up a series of thresholds. However, the interference and crosstalk between adjacent channels make its implementation impossible, because even in the absence of any fluorophore, a peak influenced by other channels could still be detected. Although using low crosstalk fluorophores may solve this issue, it will lead to a small number of applicable fluorophore candidates. Employment of machine learning (ML) is thereby a solution to the crosstalk problem and makes the application of adjacent fluorophore channels with strong crosstalk possible. In the present invention, ML is used to decode the fluorophore combinations by pattern recognition instead of isolated single threshold. Each barcode will have its specific spectrum pattern and can be decoded by corresponding machine learning algorithms.

In this example, four fluorophores were utilized with a total throughput of N×(2^C−1), where C is the number of fluorescent channels and N is the rounds of visualization cycles. With more fluorophores used, there will be exponential growth of the throughput. For example, with 7 fluorophore channels in single round, the throughput will be 127. Fluorophores with similar emission spectrum excited by different lasers or similar excitation lasers with different emission spectrum, can be used simultaneously in different imaging sequence, which increases the number of potential candidates. In this example, seven fluorophore candidates with acceptable brightness available had been used for a higher throughput probing.

Beside increasing more fluorophore channels, the mixed ratio of the fluorophores might also be adjusted. In this example, a binary mixing strategy was employed where each channel only has two conditions, namely, '0' or '1'. With a larger mix ratio number, for example, using a trinary mixing strategy, with '0', '1' and '2' for three different conditions in each channel, there will surely be higher throughput. The equation will be $N\times(R_{step}^{C}-1)$, where R step indicates the ratio step number, C indicates the fluorophore channels number, and N indicates the rounds of visualization cycles. Under the trinary mixing strategy with 7 different fluorophores, the multiplexing throughput can be significantly increased to over 10,000 by 5 rounds of visualization.

For example, when three types of fluorophores, namely fluorophore A, fluorophore B and fluorophore C were used, the existence of each fluorescence can be indicated by two statuses, namely '1' and '0', where '1' means existence and '0' means no existence of related fluorophore. Therefore, if a single particle simultaneously has fluorophore A, B, C, this fluorophore digital code will be '1 1 1', where the first '1' represents the existence of fluorophore A, the second '1' represents the existence of fluorophore B and the third '1' represents the existence of fluorophore C. Similarly, if another single particle only has fluorophores A and B, then it fluorophore digital code is '1 1 0'. Based on this coding strategy, with three types of fluorophores (N=3), a total of 7 fluorophores digital codes can be generated, namely '1 1 1', '1 1 0', '1 0 1', '0 1 1', '1 0 0', '0 1 0' and '0 0 1'. The '0 0 0' is not used since it actually appears no fluorescence. This binary coding strategy can be applied in more fluorophores with the following equations, $2^N-1$, where N is the number of fluorophores used for coding.

Other than existence of the fluorophore, more than two statuses such as brightness grading can be further encoded by introducing one more status in relation to 'fluorescence intensity'. For example, three fluorescence statuses, namely '0', '1', '2' in digital code, representing 'dark', 'half-bright', 'bright' fluorescent statuses, respectively, can be introduced. Therefore, in three fluorophore condition (N=3) and three fluorescence statuses (I=3), total of 26 fluorescence codes could be resulted. The equation can be $I^N-1$, where I indicates the number of fluorescent statuses caused by fluorescence intensity, N indicates the number of fluorophores used for coding.

(K) Machine Learning (ML) Based Decoding Algorithms

For decoding (readout and identification of the fluorescence codes), it is difficult to directly identify them based on visual observation or determination by threshold because of the overlapping of the spectrums emitted by the fluorophores. This cross-channel interference will lead to the existence of weak fluorescence in some fluorescent channel, where the corresponding fluorophore does not really exist. Besides, the differentiation of various fluorescence intensities makes this identification process even more difficult. In this regard, some common machine learning schemes were employed in this example to assist the readout and identification process. The difference among the existing machine learning models might be the accuracy, in which some might be better and more suitable for decoding these fluorescent codes than the others. For example, traditional machine learning algorithms such as linear regression, logistic regression, decision tree, SVM, Bayes and KNN, or advanced deep-learning algorithms, such as Convolutional Neural Networks (CNNs), Long Short Term Memory Networks (LSTMs), Recurrent Neural Networks (RNNs), etc. can be used.

There were mainly two groups in the ML decoding process, namely the training group and the test group as in FIG. 18. To start with, a training group dataset was prepared, including the actual fluorescence intensity distribution of all the fluorescence codes used. When synthesizing a new batch of barcodes, parts of the barcodes with known labels will be treated as training group to extract the spectral features and training the ML model as well. The spectral feature extraction includes the following steps: capture coding signals (s1901), binarization (s1902), region of interest (ROI) selection (s1903) and spectral pattern extraction (s1904). Finally, the training group signals and the test group signals are all processed using extracted filter for background noise removal (s1905). In this case, the background signal noise with the similar shape and size of the particles will be cleaned. To extract an effective filter to reveal the barcodes spectral pattern, top 10% of the final extracted signals of the training group was used to calculate the corresponding filter. The upper boundary of the filter was calculated as:

$$\text{Filter\_upper} = \bar{X} + 4 \times S,$$

where $\bar{X}$ represented the average of the top 10% signals and S was the standard deviation of the top 10% signals. The lower boundary of the filter was calculated as $$\text{Filter\_lower} = C_0 \times \bar{X},$$

where $C_0$ was a coefficient less than 1 and determined by the spectrum intensity range.

The following table (Table 3) summarizes some key differences between different FISH methods/sequencing techniques and the present invention ("Spectrum-FISH").

TABLE 3

Comparison of Spectrum-FISH with existing spatial profiling techniques:

| Technique | Theoretical throughput | Experimental Throughput | Spatial resolution | Targets | Multi-omics? | Tested Sample | Tissue type |
|---|---|---|---|---|---|---|---|
| seqFISH+ | — | 10000 | In situ | mRNA | No | Cortex, Olfactory bulb | Fixed |
| MERFISH | 2ˆN − 1 | 140 or 1001 | In situ | mRNA | No | Hundreds of human fibroblast cells | Fixed |
| osmFISH | 3 × N | 33 | In situ | mRNA | No | Cortex, hippocampus and ventricle | Fixed |
| seqFISH | FˆN | 12 | In situ | mRNA | No | MDN1-GFP yeast cells | Fixed |
| RNA SPOTS | 12ˆN | 10212 | In situ | mRNA | No | Fibroblast and stem cells | Fixed |
| Split-FISH | — | 317 | In situ | mRNA | No | Kidney, follicles, liver, and brain tissue | Fixed |
| ST | Sequencing | Sequencing | 200 μm | mRNA | No | Olfactory bulb | Frozen & permeabilized |
| Slide-seq | Sequencing | Sequencing | 10 μm | mRNA | No | Cerebellum and Olfactory bulb | Frozen & digested |
| HDST | Sequencing | Sequencing | 2 μm | mRNA | No | Main olfactory bulb | Frozen & permeabilized |
| DBiT-seq | Sequencing | Sequencing | 10 μm | mRNA, protein | Yes | Mouse embryo | Fixed |
| Spectrum-FISH | $N \times (R_{step}^{C} - 1)$ | 27 (can be up to 10000) | 2.5 μm | miRNA, m6A mRNA | Yes | Olfactory bulb | Acute slice |

Although the invention has been described in terms of certain embodiments, other embodiments apparent to those of ordinary skill in the art are also within the scope of this invention. Accordingly, the scope of the invention is intended to be defined only by the claims which follow.

What is claimed is:

1. A method of mapping spatial distribution and expression of multiple molecular targets with individual cells within a two-dimensional tissue boundary, comprising:

providing a molecular fishing system comprising an array of nanoprobes, wherein each nanoprobe is (i) functionalized with one or more molecular target fishing molecules for extracting the multiple molecular targets and (ii) crosslinked with one or more fluorescent dyes;

contacting the array of nanoprobes with a surface of an acute tissue slice at an interface where the one or more molecular target fishing molecules and the one or more fluorescent dyes are in contact with a superficial layer of the acute tissue slice;

extracting the molecular targets by the one or more molecular target fishing molecules from the acute tissue slice;

exposing the other surface of the acute tissue slice to an imprint irradiation to imprint an outline of the acute tissue slice on the array;

and removing the acute tissue slice from the array and subjecting the array to fluorescent imaging and subsequent barcoding, wherein the one or more fluorescent dyes have excitation and emission wavelengths in a range outside the imprint irradiation's spectrum and are cleavable from the nanoprobes by the imprint irradiation.

2. The method of claim 1, wherein a pixelated fluorescent pattern corresponding to the presence of the fluorescent dyes on the nanoprobes covered by the tissue is obtained during the exposure to the imprint irradiation.

3. The method of claim 1, wherein the imprint irradiation is UV irradiation.

4. The method of claim 1, wherein after contacting the array of nanoprobes with the surface of the tissue sample, a pressure is applied to the nanoprobes towards the tissue slice in order to puncture the nanoprobes into the superficial layer of the tissue for subsequent molecular target extraction.

5. The method of claim 1, wherein an image of the tissue and relative position of the nanoprobes are captured as a spatial registration of one or more cell types in the tissue associated with the nanoprobes prior to the removal of the tissue sample from the array.

6. The method of claim 5, wherein the one or more cell types in the tissue associated with the nanoprobes are labelled by immunostaining with specific markers.

7. The method of claim 6, wherein the subsequent barcoding is performed by subjecting the array of nanoprobes to a plurality of reporter sequences complementary to the molecular targets extracted by the nanoprobes, wherein each of the reporter sequences is associated with a pre-determined mix ratio of multiple labelling agents for spectral analysis.

* * * * *

SEQUENCE LISTING

```
Sequence total quantity: 66
SEQ ID NO: 1             moltype = RNA  length = 32
FEATURE                  Location/Qualifiers
source                   1..32
                         mol_type = other RNA
                         organism = synthetic construct
misc_feature             1..32
                         note = mmu-miR-124-3p probe sequence
SEQUENCE: 1
ggcattcacc gcgtgcctta cgccacgtgt tc                                32

SEQ ID NO: 2             moltype = DNA  length = 18
FEATURE                  Location/Qualifiers
source                   1..18
                         mol_type = other DNA
                         organism = synthetic construct
misc_feature             1..18
                         note = mmu-miR-124-3p reporter sequence
SEQUENCE: 2
ttttttgaac acgtggcg                                                18

SEQ ID NO: 3             moltype = RNA  length = 33
FEATURE                  Location/Qualifiers
source                   1..33
                         mol_type = other RNA
                         organism = synthetic construct
misc_feature             1..33
                         note = mmu-miR-128-3p probe sequence
SEQUENCE: 3
aaagagaccg gttcactgtg agttaactgt tga                               33

SEQ ID NO: 4             moltype = DNA  length = 18
FEATURE                  Location/Qualifiers
source                   1..18
```

```
                        mol_type = other DNA
                        organism = synthetic construct
misc_feature            1..18
                        note = mmu-miR-128-3p reporter sequence
SEQUENCE: 4
ttttttcaa cagttaac                                              18

SEQ ID NO: 5            moltype = RNA  length = 33
FEATURE                 Location/Qualifiers
source                  1..33
                        mol_type = other RNA
                        organism = synthetic construct
misc_feature            1..33
                        note = mmu-miR-29b-3p probe sequence
SEQUENCE: 5
cactgatttc aaatggtgct attggtggca cat                            33

SEQ ID NO: 6            moltype = DNA  length = 18
FEATURE                 Location/Qualifiers
source                  1..18
                        mol_type = other DNA
                        organism = synthetic construct
misc_feature            1..18
                        note = mmu-miR-29b-3p reporter sequence
SEQUENCE: 6
ttttttatgt gccaccaa                                             18

SEQ ID NO: 7            moltype = RNA  length = 33
FEATURE                 Location/Qualifiers
source                  1..33
                        mol_type = other RNA
                        organism = synthetic construct
misc_feature            1..33
                        note = mmu-miR-9-5p probe sequence
SEQUENCE: 7
atacagctag ataaccaaag aaagtaatac cat                            33

SEQ ID NO: 8            moltype = DNA  length = 18
FEATURE                 Location/Qualifiers
source                  1..18
                        mol_type = other DNA
                        organism = synthetic construct
misc_feature            1..18
                        note = mmu-miR-9-5p reporter sequence
SEQUENCE: 8
ttttttatgg tattactt                                             18

SEQ ID NO: 9            moltype = RNA  length = 33
FEATURE                 Location/Qualifiers
source                  1..33
                        mol_type = other RNA
                        organism = synthetic construct
misc_feature            1..33
                        note = mmu-miR-29a-3p probe sequence
SEQUENCE: 9
aaccgatttc agatggtgct aggtccctca aat                            33

SEQ ID NO: 10           moltype = DNA  length = 18
FEATURE                 Location/Qualifiers
source                  1..18
                        mol_type = other DNA
                        organism = synthetic construct
misc_feature            1..18
                        note = mmu-miR-29a-3p reporter sequence
SEQUENCE: 10
ttttttattt gagggacc                                             18

SEQ ID NO: 11           moltype = RNA  length = 33
FEATURE                 Location/Qualifiers
source                  1..33
                        mol_type = other RNA
                        organism = synthetic construct
misc_feature            1..33
                        note = mmu-miR-22-3p probe sequence
SEQUENCE: 11
cagttcttca actggcagct tcatgctagc gtg                            33

SEQ ID NO: 12           moltype = DNA  length = 18
FEATURE                 Location/Qualifiers
```

```
source                  1..18
                        mol_type = other DNA
                        organism = synthetic construct
misc_feature            1..18
                        note = mmu-miR-22-3p reporter sequence
SEQUENCE: 12
ttttttcacg ctagcatg                                            18

SEQ ID NO: 13           moltype = RNA  length = 33
FEATURE                 Location/Qualifiers
source                  1..33
                        mol_type = other RNA
                        organism = synthetic construct
misc_feature            1..33
                        note = mmu-let-7c-5p probe sequence
SEQUENCE: 13
accatacaac ctactacctc agctatccat atg                           33

SEQ ID NO: 14           moltype = DNA  length = 18
FEATURE                 Location/Qualifiers
source                  1..18
                        mol_type = other DNA
                        organism = synthetic construct
misc_feature            1..18
                        note = mmu-let-7c-5p reporter sequence
SEQUENCE: 14
ttttttcata tggatagc                                            18

SEQ ID NO: 15           moltype = RNA  length = 33
FEATURE                 Location/Qualifiers
source                  1..33
                        mol_type = other RNA
                        organism = synthetic construct
misc_feature            1..33
                        note = mmu-miR-26a-5p probe sequence
SEQUENCE: 15
gcctatcctg gattacttga agtccacagg aca                           33

SEQ ID NO: 16           moltype = DNA  length = 18
FEATURE                 Location/Qualifiers
source                  1..18
                        mol_type = other DNA
                        organism = synthetic construct
misc_feature            1..18
                        note = mmu-miR-26a-5p reporter sequence
SEQUENCE: 16
tttttttgtc ctgtggac                                            18

SEQ ID NO: 17           moltype = RNA  length = 33
FEATURE                 Location/Qualifiers
source                  1..33
                        mol_type = other RNA
                        organism = synthetic construct
misc_feature            1..33
                        note = mmu-let-7f-5p probe sequence
SEQUENCE: 17
actatacaat ctactacctc aggatttacc ctt                           33

SEQ ID NO: 18           moltype = DNA  length = 18
FEATURE                 Location/Qualifiers
source                  1..18
                        mol_type = other DNA
                        organism = synthetic construct
misc_feature            1..18
                        note = mmu-let-7f-5p reporter sequence
SEQUENCE: 18
ttttttaagg gtaaatcc                                            18

SEQ ID NO: 19           moltype = RNA  length = 33
FEATURE                 Location/Qualifiers
source                  1..33
                        mol_type = other RNA
                        organism = synthetic construct
misc_feature            1..33
                        note = mmu-let-7a-5p probe sequence
SEQUENCE: 19
actatacaac ctactacctc atatgcgccg gtt                           33

SEQ ID NO: 20           moltype = DNA  length = 18
```

```
FEATURE                 Location/Qualifiers
source                  1..18
                        mol_type = other DNA
                        organism = synthetic construct
misc_feature            1..18
                        note = mmu-let-7a-5p reporter sequence
SEQUENCE: 20
ttttttaacc ggcgcata                                            18

SEQ ID NO: 21           moltype = RNA  length = 33
FEATURE                 Location/Qualifiers
source                  1..33
                        mol_type = other RNA
                        organism = synthetic construct
misc_feature            1..33
                        note = mmu-let-7g-5p probe sequence
SEQUENCE: 21
actgtacaaa ctactacctc attcagccac gct                           33

SEQ ID NO: 22           moltype = DNA  length = 18
FEATURE                 Location/Qualifiers
source                  1..18
                        mol_type = other DNA
                        organism = synthetic construct
misc_feature            1..18
                        note = mmu-let-7g-5p reporter sequence
SEQUENCE: 22
ttttttagcg tggctgaa                                            18

SEQ ID NO: 23           moltype = RNA  length = 33
FEATURE                 Location/Qualifiers
source                  1..33
                        mol_type = other RNA
                        organism = synthetic construct
misc_feature            1..33
                        note = mmu-let-7b-5p probe sequence
SEQUENCE: 23
accacacaac ctactacctc atatgcccag cat                           33

SEQ ID NO: 24           moltype = DNA  length = 18
FEATURE                 Location/Qualifiers
source                  1..18
                        mol_type = other DNA
                        organism = synthetic construct
misc_feature            1..18
                        note = mmu-let-7b-5p reporter sequence
SEQUENCE: 24
ttttttatgc tgggcata                                            18

SEQ ID NO: 25           moltype = RNA  length = 33
FEATURE                 Location/Qualifiers
source                  1..33
                        mol_type = other RNA
                        organism = synthetic construct
misc_feature            1..33
                        note = mmu-miR-29c-3p probe sequence
SEQUENCE: 25
aaccgatttc aaatggtgct acgttacaac cag                           33

SEQ ID NO: 26           moltype = DNA  length = 18
FEATURE                 Location/Qualifiers
source                  1..18
                        mol_type = other DNA
                        organism = synthetic construct
misc_feature            1..18
                        note = mmu-miR-29c-3p reporter sequence
SEQUENCE: 26
ttttttctgg ttgtaacg                                            18

SEQ ID NO: 27           moltype = RNA  length = 33
FEATURE                 Location/Qualifiers
source                  1..33
                        mol_type = other RNA
                        organism = synthetic construct
misc_feature            1..33
                        note = mmu-miR-181a-5p probe sequence
SEQUENCE: 27
tcaccgacag cgttgaatgt taccgatact aga                           33
```

```
SEQ ID NO: 28          moltype = DNA  length = 18
FEATURE                Location/Qualifiers
source                 1..18
                       mol_type = other DNA
                       organism = synthetic construct
misc_feature           1..18
                       note = mmu-miR-181a-5p reporter sequence
SEQUENCE: 28
tttttttcta gtatcggt                                          18

SEQ ID NO: 29          moltype = RNA  length = 33
FEATURE                Location/Qualifiers
source                 1..33
                       mol_type = other RNA
                       organism = synthetic construct
misc_feature           1..33
                       note = mmu-miR-376a-3p probe sequence
SEQUENCE: 29
acgtggattt tcctctacga ttgtataaag tcc                         33

SEQ ID NO: 30          moltype = DNA  length = 18
FEATURE                Location/Qualifiers
source                 1..18
                       mol_type = other DNA
                       organism = synthetic construct
misc_feature           1..18
                       note = mmu-miR-376a-3p reporter sequence
SEQUENCE: 30
ttttttggac tttataca                                          18

SEQ ID NO: 31          moltype = RNA  length = 33
FEATURE                Location/Qualifiers
source                 1..33
                       mol_type = other RNA
                       organism = synthetic construct
misc_feature           1..33
                       note = mmu-miR-99a-5p probe sequence
SEQUENCE: 31
acaagatcgg atctacgggt tgccatgcag acg                         33

SEQ ID NO: 32          moltype = DNA  length = 18
FEATURE                Location/Qualifiers
source                 1..18
                       mol_type = other DNA
                       organism = synthetic construct
misc_feature           1..18
                       note = mmu-miR-99a-5p reporter sequence
SEQUENCE: 32
ttttttcgtc tgcatggc                                          18

SEQ ID NO: 33          moltype = RNA  length = 33
FEATURE                Location/Qualifiers
source                 1..33
                       mol_type = other RNA
                       organism = synthetic construct
misc_feature           1..33
                       note = mmu-let-7d-5p probe sequence
SEQUENCE: 33
actatgcaac ctactacctc tgattaccga gca                         33

SEQ ID NO: 34          moltype = DNA  length = 18
FEATURE                Location/Qualifiers
source                 1..18
                       mol_type = other DNA
                       organism = synthetic construct
misc_feature           1..18
                       note = mmu-let-7d-5p reporter sequence
SEQUENCE: 34
tttttttgct cggtaatc                                          18

SEQ ID NO: 35          moltype = RNA  length = 33
FEATURE                Location/Qualifiers
source                 1..33
                       mol_type = other RNA
                       organism = synthetic construct
misc_feature           1..33
                       note = mmu-miR-137-3p probe sequence
SEQUENCE: 35
acgcgtattc ttaagcaata attctatcag gtc                         33
```

```
SEQ ID NO: 36           moltype = DNA  length = 18
FEATURE                 Location/Qualifiers
source                  1..18
                        mol_type = other DNA
                        organism = synthetic construct
misc_feature            1..18
                        note = mmu-miR-137-3p reporter sequence
SEQUENCE: 36
tttttgacc tgatagaa                                              18

SEQ ID NO: 37           moltype = RNA  length = 33
FEATURE                 Location/Qualifiers
source                  1..33
                        mol_type = other RNA
                        organism = synthetic construct
misc_feature            1..33
                        note = mmu-let-7e-5p probe sequence
SEQUENCE: 37
actatacaac ctcctacctc aggcgaccac tag                            33

SEQ ID NO: 38           moltype = DNA  length = 18
FEATURE                 Location/Qualifiers
source                  1..18
                        mol_type = other DNA
                        organism = synthetic construct
misc_feature            1..18
                        note = mmu-let-7e-5p reporter sequence
SEQUENCE: 38
ttttttctag tggtcgcc                                             18

SEQ ID NO: 39           moltype = RNA  length = 33
FEATURE                 Location/Qualifiers
source                  1..33
                        mol_type = other RNA
                        organism = synthetic construct
misc_feature            1..33
                        note = mmu-miR-125b-5p probe sequence
SEQUENCE: 39
cacaagttag ggtctcaggg atgagctact gga                            33

SEQ ID NO: 40           moltype = DNA  length = 18
FEATURE                 Location/Qualifiers
source                  1..18
                        mol_type = other DNA
                        organism = synthetic construct
misc_feature            1..18
                        note = mmu-miR-125b-5p reporter sequence
SEQUENCE: 40
tttttttcca gtagctca                                             18

SEQ ID NO: 41           moltype = RNA  length = 33
FEATURE                 Location/Qualifiers
source                  1..33
                        mol_type = other RNA
                        organism = synthetic construct
misc_feature            1..33
                        note = mmu-miR-369-3p probe sequence
SEQUENCE: 41
aaagatcaac catgtattat tgccgagggg taa                            33

SEQ ID NO: 42           moltype = DNA  length = 18
FEATURE                 Location/Qualifiers
source                  1..18
                        mol_type = other DNA
                        organism = synthetic construct
misc_feature            1..18
                        note = mmu-miR-369-3p reporter sequence
SEQUENCE: 42
ttttttttac ccctcggc                                             18

SEQ ID NO: 43           moltype = RNA  length = 33
FEATURE                 Location/Qualifiers
source                  1..33
                        mol_type = other RNA
                        organism = synthetic construct
misc_feature            1..33
                        note = mmu-miR-30a-5p probe sequence
SEQUENCE: 43
```

```
ttccagtcga ggatgtttac accacgatgc cgc                                33

SEQ ID NO: 44           moltype = DNA  length = 18
FEATURE                 Location/Qualifiers
source                  1..18
                        mol_type = other DNA
                        organism = synthetic construct
misc_feature            1..18
                        note = mmu-miR-30a-5p reporter sequence
SEQUENCE: 44
tttttgcgg catcgtgg                                                  18

SEQ ID NO: 45           moltype = RNA  length = 33
FEATURE                 Location/Qualifiers
source                  1..33
                        mol_type = other RNA
                        organism = synthetic construct
misc_feature            1..33
                        note = mmu-miR-127-3p probe sequence
SEQUENCE: 45
gccaagctca gacggatccg ataagaacct ctc                                33

SEQ ID NO: 46           moltype = DNA  length = 18
FEATURE                 Location/Qualifiers
source                  1..18
                        mol_type = other DNA
                        organism = synthetic construct
misc_feature            1..18
                        note = mmu-miR-127-3p reporter sequence
SEQUENCE: 46
ttttttgaga ggttctta                                                 18

SEQ ID NO: 47           moltype = RNA  length = 33
FEATURE                 Location/Qualifiers
source                  1..33
                        mol_type = other RNA
                        organism = synthetic construct
misc_feature            1..33
                        note = mmu-miR-138-5p probe sequence
SEQUENCE: 47
gcctgattca caacaccagc tggtcgacgc aag                                33

SEQ ID NO: 48           moltype = DNA  length = 18
FEATURE                 Location/Qualifiers
source                  1..18
                        mol_type = other DNA
                        organism = synthetic construct
misc_feature            1..18
                        note = mmu-miR-138-5p reporter sequence
SEQUENCE: 48
ttttttcttg cgtcgacc                                                 18

SEQ ID NO: 49           moltype = RNA  length = 41
FEATURE                 Location/Qualifiers
source                  1..41
                        mol_type = mRNA
                        organism = Mus musculus
modified_base           21
                        mod_base = m6a
misc_binding            24..41
                        bound_moiety = Captured By Reporter Sequence
misc_feature            1..41
                        note = Myo16-m6A reference sequence
SEQUENCE: 49
cacctccttt gtttttagag actcgaaaag ccatcatctt g                       41

SEQ ID NO: 50           moltype = DNA  length = 30
FEATURE                 Location/Qualifiers
source                  1..30
                        mol_type = other DNA
                        organism = synthetic construct
repeat_region           1..12
                        note = 5'-repeat
misc_feature            1..30
                        note = Myo16-m6A reporter sequence
SEQUENCE: 50
aaactacgat ggcaagatga tggcttttcg                                    30

SEQ ID NO: 51           moltype = RNA  length = 41
```

```
FEATURE                 Location/Qualifiers
source                  1..41
                        mol_type = mRNA
                        organism = Mus musculus
modified_base           21
                        mod_base = m6a
misc_binding            24..41
                        bound_moiety = Capture By Reporter Sequence
misc_feature            1..41
                        note = Gng4-m6A reference sequence
SEQUENCE: 51
aagccttgag attttccatg acaaggctgt tggccccatc t                        41

SEQ ID NO: 52           moltype = DNA  length = 30
FEATURE                 Location/Qualifiers
source                  1..30
                        mol_type = other DNA
                        organism = synthetic construct
repeat_region           1..12
                        note = 5'-repeat
misc_feature            1..30
                        note = Gng4-m6A reporter sequence
SEQUENCE: 52
aaactacgat ggagatgggg ccaacagcct                                     30

SEQ ID NO: 53           moltype = RNA  length = 41
FEATURE                 Location/Qualifiers
source                  1..41
                        mol_type = mRNA
                        organism = Mus musculus
modified_base           21
                        mod_base = m6a
misc_binding            24..41
                        bound_moiety = Captured By Reporter Sequence
misc_feature            1..41
                        note = Fam184a-m6A reference sequence
SEQUENCE: 53
gctggcacag ctctgtgtgg actgttccaa gagcatgact g                        41

SEQ ID NO: 54           moltype = DNA  length = 30
FEATURE                 Location/Qualifiers
source                  1..30
                        mol_type = other DNA
                        organism = synthetic construct
repeat_region           1..12
                        note = 5'-repeat
misc_feature            1..30
                        note = Fam184a-m6A reporter sequence
SEQUENCE: 54
aaactacgat ggcagtcatg ctcttggaac                                     30

SEQ ID NO: 55           moltype = RNA  length = 41
FEATURE                 Location/Qualifiers
source                  1..41
                        mol_type = mRNA
                        organism = Mus musculus
modified_base           21
                        mod_base = m6a
misc_binding            24..41
                        bound_moiety = Captured by Reporter Sequence
misc_feature            1..41
                        note = Nmb-m6A reference sequence
SEQUENCE: 55
gtgtccatcc agggaagctg acaatggaac cctagcagtg g                        41

SEQ ID NO: 56           moltype = DNA  length = 30
FEATURE                 Location/Qualifiers
source                  1..30
                        mol_type = other DNA
                        organism = synthetic construct
repeat_region           1..12
                        note = 5'-repeat
misc_feature            1..30
                        note = Nmb-m6A reporter sequence
SEQUENCE: 56
aaactacgat ggccactgct agggttccat                                     30

SEQ ID NO: 57           moltype = RNA  length = 41
FEATURE                 Location/Qualifiers
```

-continued

```
source                1..41
                      mol_type = mRNA
                      organism = Mus musculus
modified_base         21
                      mod_base = m6a
misc_binding          24..41
                      bound_moiety = Captured by Reporter Sequence
misc_feature          1..41
                      note = Gcnt1-m6A reference sequence
SEQUENCE: 57
gaggcataaa gccctggaga acttagaaca ctaagcgctg c                    41

SEQ ID NO: 58         moltype = DNA  length = 30
FEATURE               Location/Qualifiers
source                1..30
                      mol_type = other DNA
                      organism = synthetic construct
repeat_region         1..12
                      note = 5'-repeat
misc_feature          1..30
                      note = Gcnt1-m6A reporter sequence
SEQUENCE: 58
aaactacgat gggcagcgct tagtgttcta                                 30

SEQ ID NO: 59         moltype = RNA  length = 41
FEATURE               Location/Qualifiers
source                1..41
                      mol_type = mRNA
                      organism = Mus musculus
modified_base         21
                      mod_base = m6a
misc_binding          24..41
                      bound_moiety = Captured by Reporter Sequence
misc_feature          1..41
                      note = Prox1-m6A reference sequence
SEQUENCE: 59
cggctccttc tcggggaagg acagagcctc tcctgagtcc t                    41

SEQ ID NO: 60         moltype = DNA  length = 30
FEATURE               Location/Qualifiers
source                1..30
                      mol_type = other DNA
                      organism = synthetic construct
repeat_region         1..12
                      note = 5'-repeat
misc_feature          1..30
                      note = Prox1-m6A reporter sequence
SEQUENCE: 60
aaactacgat ggaggactca ggagaggctc                                 30

SEQ ID NO: 61         moltype = RNA  length = 41
FEATURE               Location/Qualifiers
source                1..41
                      mol_type = mRNA
                      organism = Mus musculus
modified_base         21
                      mod_base = m6a
misc_binding          24..41
                      bound_moiety = Captured by Reporter Sequence
misc_feature          1..41
                      note = Gpr161-m6A reference sequence
SEQUENCE: 61
tgccaccctc tgatctacgg actctggaac aagactgtgc g                    41

SEQ ID NO: 62         moltype = DNA  length = 30
FEATURE               Location/Qualifiers
source                1..30
                      mol_type = other DNA
                      organism = synthetic construct
repeat_region         1..12
                      note = 5'-repeat
misc_feature          1..30
                      note = Gpr161-m6A reporter sequence
SEQUENCE: 62
aaactacgat ggcgcacagt cttgttccag                                 30

SEQ ID NO: 63         moltype = RNA  length = 41
FEATURE               Location/Qualifiers
source                1..41
```

-continued

```
                        mol_type = mRNA
                        organism = Mus musculus
modified_base           21
                        mod_base = m6a
misc_binding            24..41
                        bound_moiety = Captured by Reporter Sequence
misc_feature            1..41
                        note = Epha7-m6A reference sequence
SEQUENCE: 63
tggccaggaa cacagcagag acaataaaca aagtactacc t                       41

SEQ ID NO: 64           moltype = DNA  length = 30
FEATURE                 Location/Qualifiers
source                  1..30
                        mol_type = other DNA
                        organism = synthetic construct
repeat_region           1..12
                        note = 5'-repeat
misc_feature            1..30
                        note = Epha7-m6A reporter sequence
SEQUENCE: 64
aaactacgat ggaggtagta ctttgtttat                                    30

SEQ ID NO: 65           moltype = RNA  length = 41
FEATURE                 Location/Qualifiers
source                  1..41
                        mol_type = mRNA
                        organism = Mus musculus
modified_base           21
                        mod_base = m6a
misc_binding            24..41
                        bound_moiety = Captured by Reporter Sequence
misc_feature            1..41
                        note = Zbtb20-m6A reference sequence
SEQUENCE: 65
aacgacaaca aaagaaataa acaagcaaac aaacagacaa a                       41

SEQ ID NO: 66           moltype = DNA  length = 30
FEATURE                 Location/Qualifiers
source                  1..30
                        mol_type = other DNA
                        organism = synthetic construct
repeat_region           1..12
                        note = 5'-repeat
misc_feature            1..30
                        note = Zbtb20-m6A reporter sequence
SEQUENCE: 66
aaactacgat ggtttgtctg tttgtttgct                                    30
```